(12) United States Patent
Bush et al.

(10) Patent No.: US 8,318,171 B2
(45) Date of Patent: Nov. 27, 2012

(54) NEUROTOXIC OLIGOMERS

(75) Inventors: Ashley Bush, Somerville, MA (US); Robert Cherny, Brighton East (AU)

(73) Assignees: Prana Biotechnology Limited, Victoria (AU); The General Hospital Corporation, Boston, MA (US)

( * ) Notice: Subject to any disclaimer, the term of this patent is extended or adjusted under 35 U.S.C. 154(b) by 415 days.

(21) Appl. No.: 12/466,094

(22) Filed: May 14, 2009

(65) Prior Publication Data

US 2009/0297538 A1    Dec. 3, 2009

Related U.S. Application Data

(62) Division of application No. 10/312,437, filed as application No. PCT/AU01/00786 on Jun. 28, 2001, now Pat. No. 7,618,634.

(60) Provisional application No. 60/242,177, filed on Oct. 23, 2000, provisional application No. 60/214,779, filed on Jun. 28, 2000.

(51) Int. Cl.
  *A61K 39/395* (2006.01)
(52) U.S. Cl. .................................................. 424/172.1
(58) Field of Classification Search .................. None
  See application file for complete search history.

(56) References Cited

U.S. PATENT DOCUMENTS

| | | | |
|---|---|---|---|
| 4,863,735 A | 9/1989 | Kohn et al. | 424/422 |
| 5,688,651 A | 11/1997 | Solomon | 435/7.1 |

FOREIGN PATENT DOCUMENTS

WO    WO 9927944 A1    6/1999

OTHER PUBLICATIONS

Zhou et al. Comparison of Freund's adjuvant and TiterMax in inducing anti-idiotype to idiotypic antibodies against pseudorabies virus antigens. Vet Immunol Immunopathol. Sep. 1995;48(1-2):113-22.*
Chiang et al. The many faces of amyloid beta in Alzheimer's disease. Curr Mol Med. Sep. 2008;8(6):580-4.*
Matsunaga et al. Eight-residue Abeta peptides inhibit the aggregation and enzymatic activity of Abeta42. Regul Pept. Aug. 15, 2004;120(1-3):227-36.*
Schenk D. et al., "Immunization with Amyloid-β Attenuates Alzheimer-Disease-Like Pathology in the PDAPP Mouse", *Nature*, 400:173-177 (1999).
Galeazzi L. et al., "In Vitro Peroxidase Oxidation Induces Stable Dimers of β-Amyloid (1-42) Through Dityrosine Bridge Formation", *Amyloid: The Int. J. Exp. And Clin. Invest.*,6(1):7-13 (1999).
Atwood C.S. et al., "Dramatic Aggregation of Alzheimer's Aβ by Cu(II) is Induced by Conditions Representing Physiological Acidosis", *The Journal of Biological Chemistry*, 273(21):12817-12826 (1998).
Vickers, "A vaccine against Alzheimer's disease: developments to date", Drugs Aging 19(7): 487-494 (2002).
Perez et al., "The beta-amyloid precursor protein of Alzheimer's disease enhances neuron viability and modulates neuronal polarity", J Neurosci, 17(24): 9407-9414 (1997).
Liu et al., "Amyliod beta peptide alters intracellular vesicle trafficking and cholesterol homeostasis", Proc Natl Sci USA, 95(22): 13266-13271 (1998).
Casadesus et al., "The estrogen myth: potential use of gonadotropin-releasing hormone agonists for the treatment of Alzheimer's disease", Drugs in R&D 7(3): 187-193 (2006).
Jacob J.S. et al., "Human Phagocytes Employ the Myeloperoxidase-Hydrogen Peroxide System to Synthesize Dityrosine, Trityrosine, Pulcherosine, and Isodityrosine by a Tyrosyl Radical-Dependent Pathway", *The Journal of Biological Chemistry*, 271(33):19950-19956 (1996).
Souza J.M. et al., "Dityrosine Cross-Linking Promotes Formation of Stable α-Synuclein Polymers", *The Journal of Biological Chemistry*, 275(24):18344-18349 (2000).
McLean C.A. et al., "Soluble Pool of Aβ Amyloid as a Determinant of Severity of Neurodegeneration in Alzheimer's Disease", *Annals Neurolgy*, 46(6):860-866 (1999).
Hock C. et al., "Cerebrospinal Fluid Levels of Amyloid Precursor Protein and Amyloid β-Peptide in Alzheimer's Disease and Major Depression-Inverse Correlation with Dementia Severity", *Eur. Neural*, 39:111-118 (1998).
Atwood C.S. et al., "Role of Free Radicals and Metal Ions in the Pathogenesis of Alzheimer's Disease", *Metal Ions in Biological Systems*, 36:309-364 (1999).
Kato Y. et al., "Immunohistochemical Detection of Dityrosine in Lipofuscin Pigments in the Aged Human Brain", *FEBS Letters*, 439:231-234 (1998).
Kotilinek, L.A. et al., "Reversible Memory Loss in a Mouse Transgenic Model of Alzheimer's Disease" Journal of Neuroscience (Aug. 1, 2002) pp. 6331-6335, vol. 22, No. 14.

* cited by examiner

*Primary Examiner* — Gregory S Emch
(74) *Attorney, Agent, or Firm* — Scully, Scott, Murphy & Presser, P.C.

(57) ABSTRACT

This invention relates to methods and compositions for the treatment or alleviation of Alzheimer's disease and of other conditions related to abnormal protein aggregation. In particular, the invention relates to methods and compositions for the immunotherapy of Alzheimer's disease, Parkinson's disease, and cataract. In one aspect the invention provides a method of prophylaxis, treatment or alleviation of a condition characterized by pathological aggregation and accumulation of a specific protein associated with an immunizing-effective dose of one or more tyrosine cross-linked compounds, and optionally also comprising copper ions complexed to the compound. Alternatively passive immunization against a tyrosine cross-linked compound may be used. Prophylactic or therapeutic compositions and diagnostic methods are also disclosed and claimed.

1 Claim, 19 Drawing Sheets

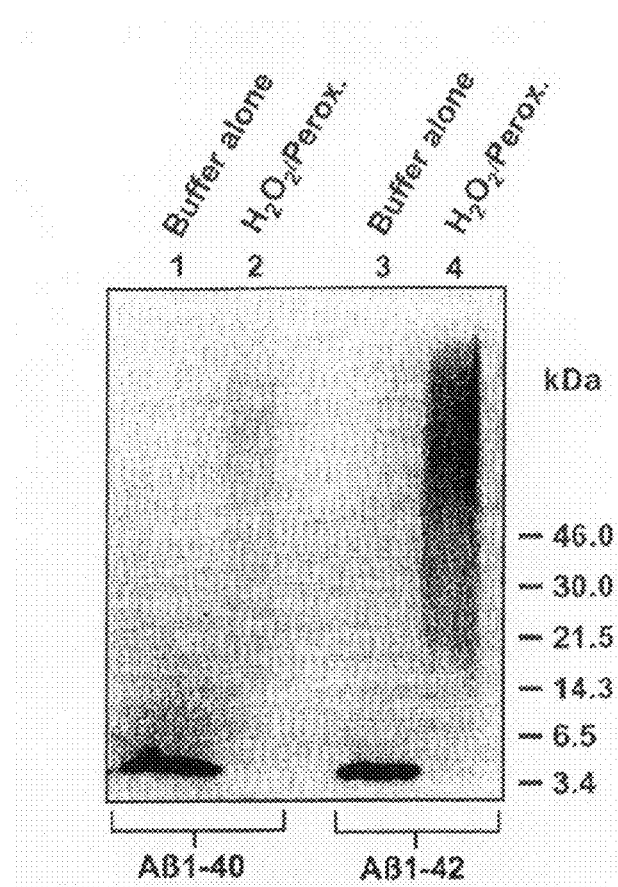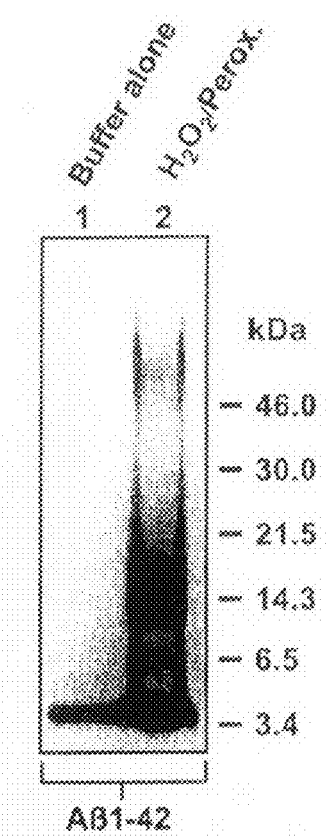
Fig. 1B
Fig. 1C

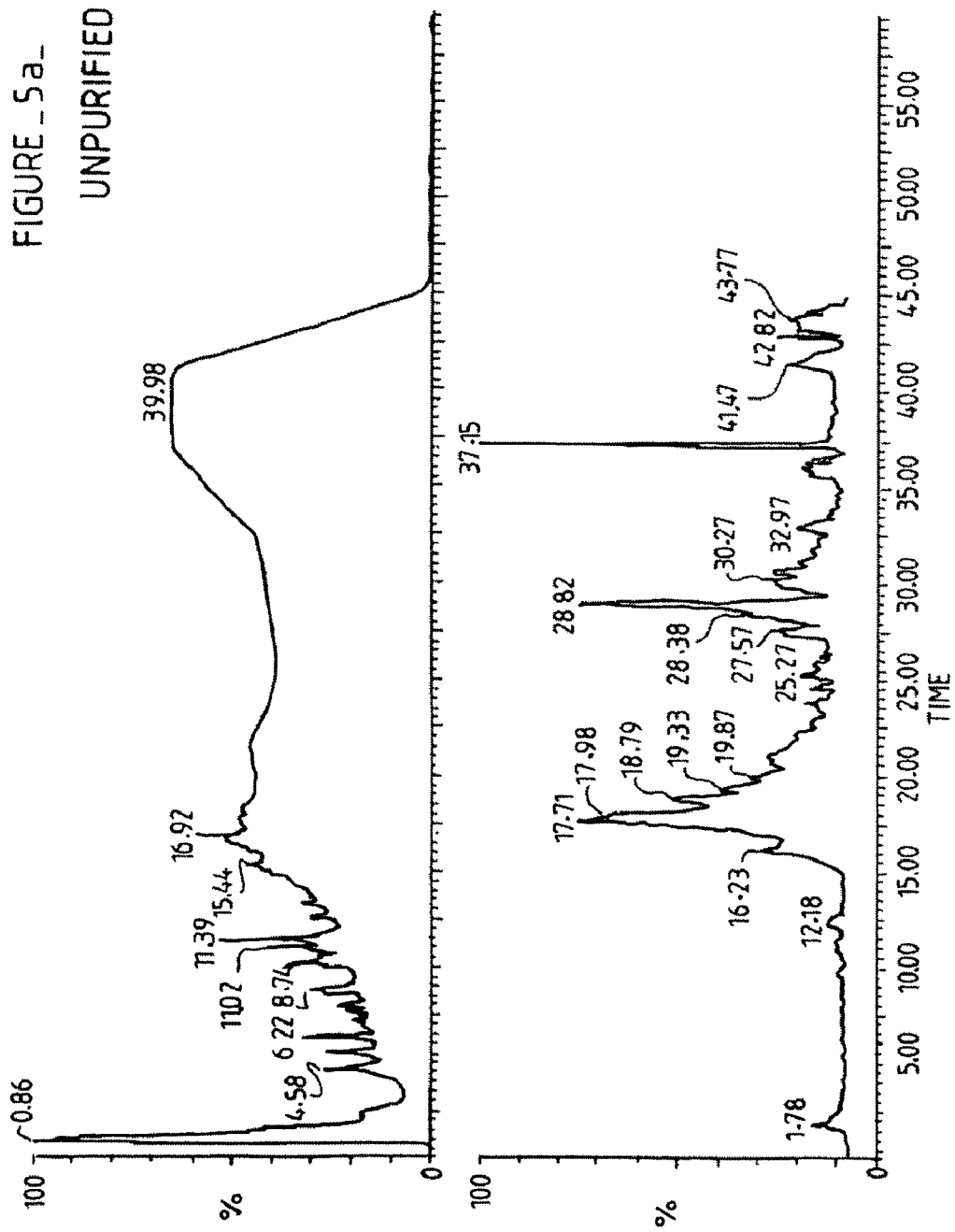
FIGURE_5a_ UNPURIFIED

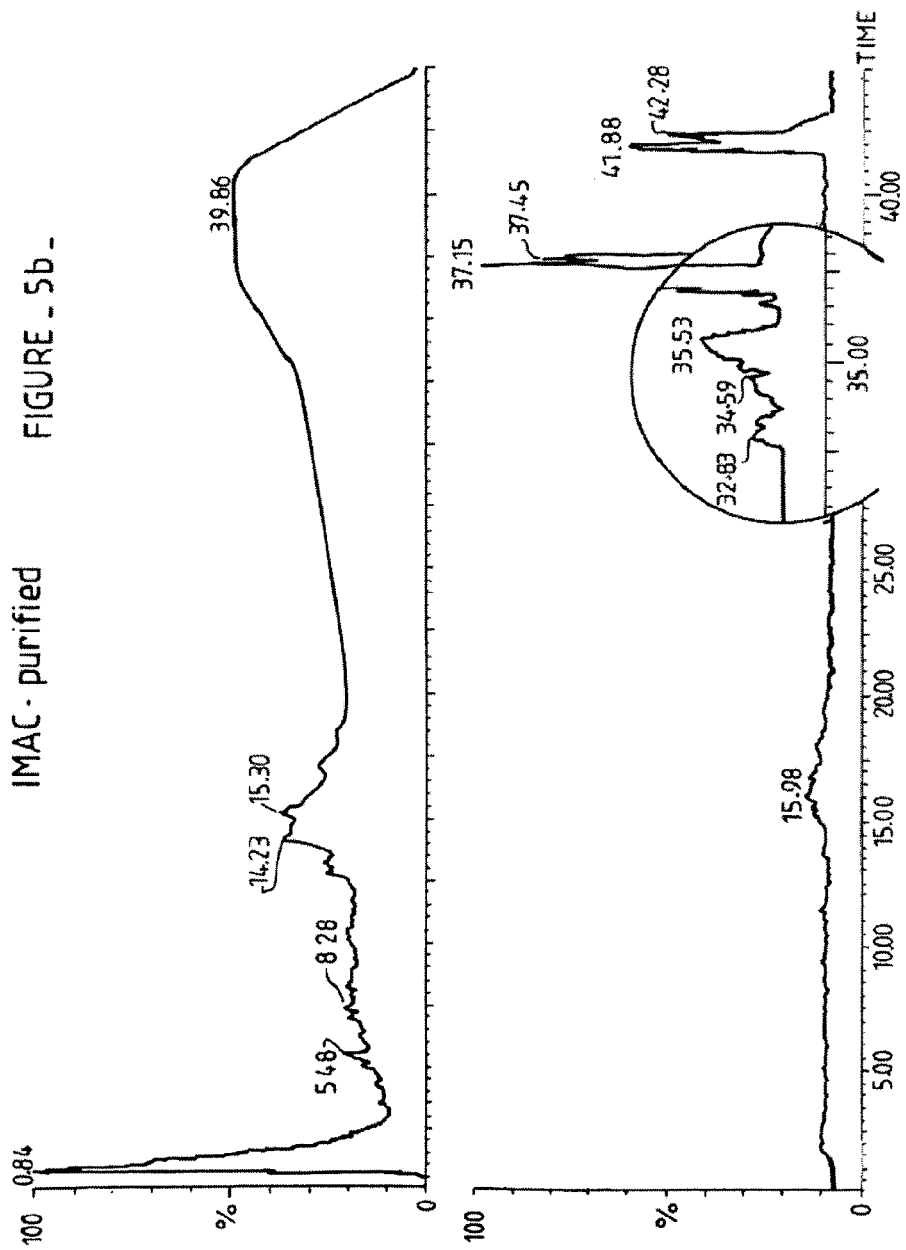
FIGURE_5b_ IMAC - purified

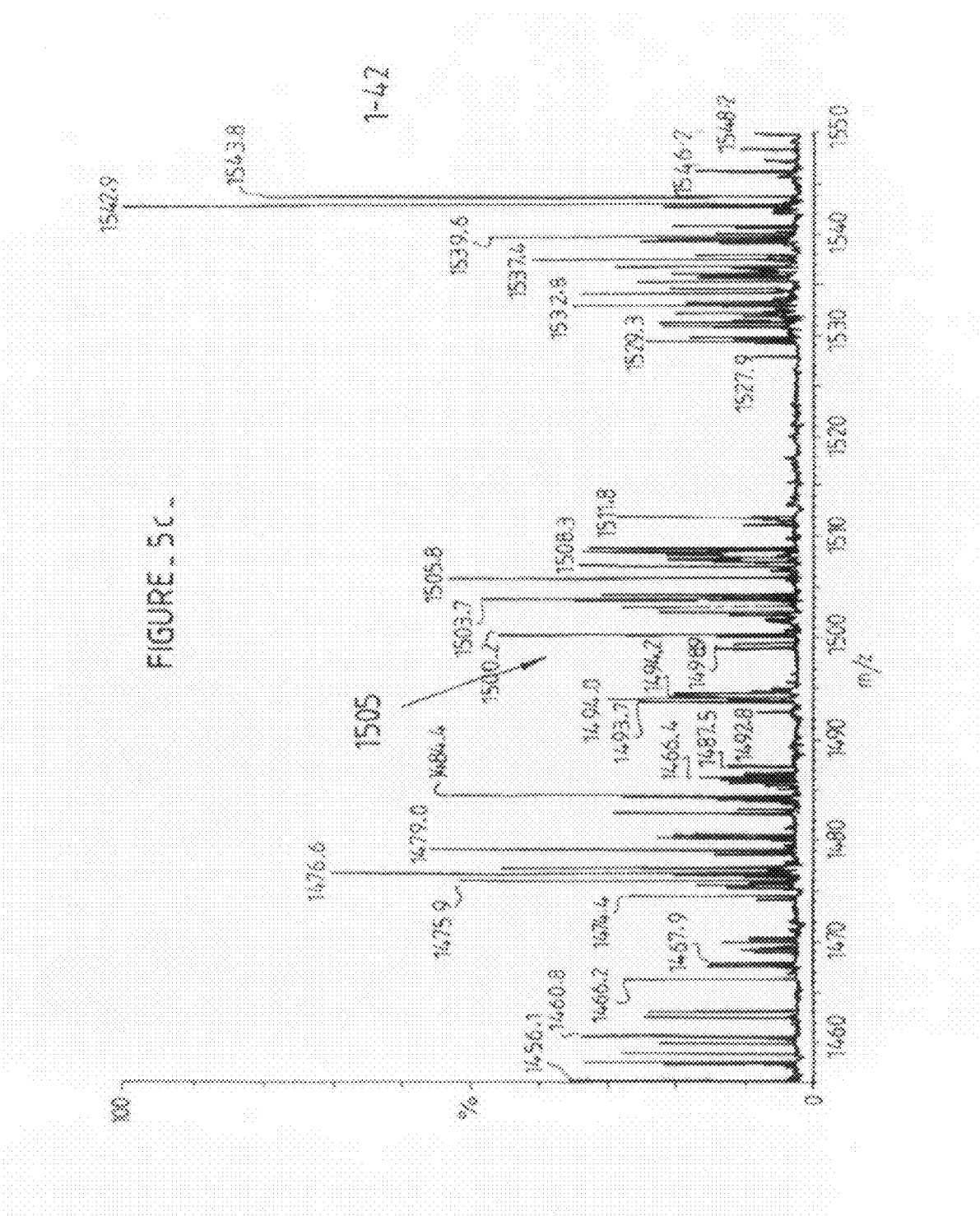

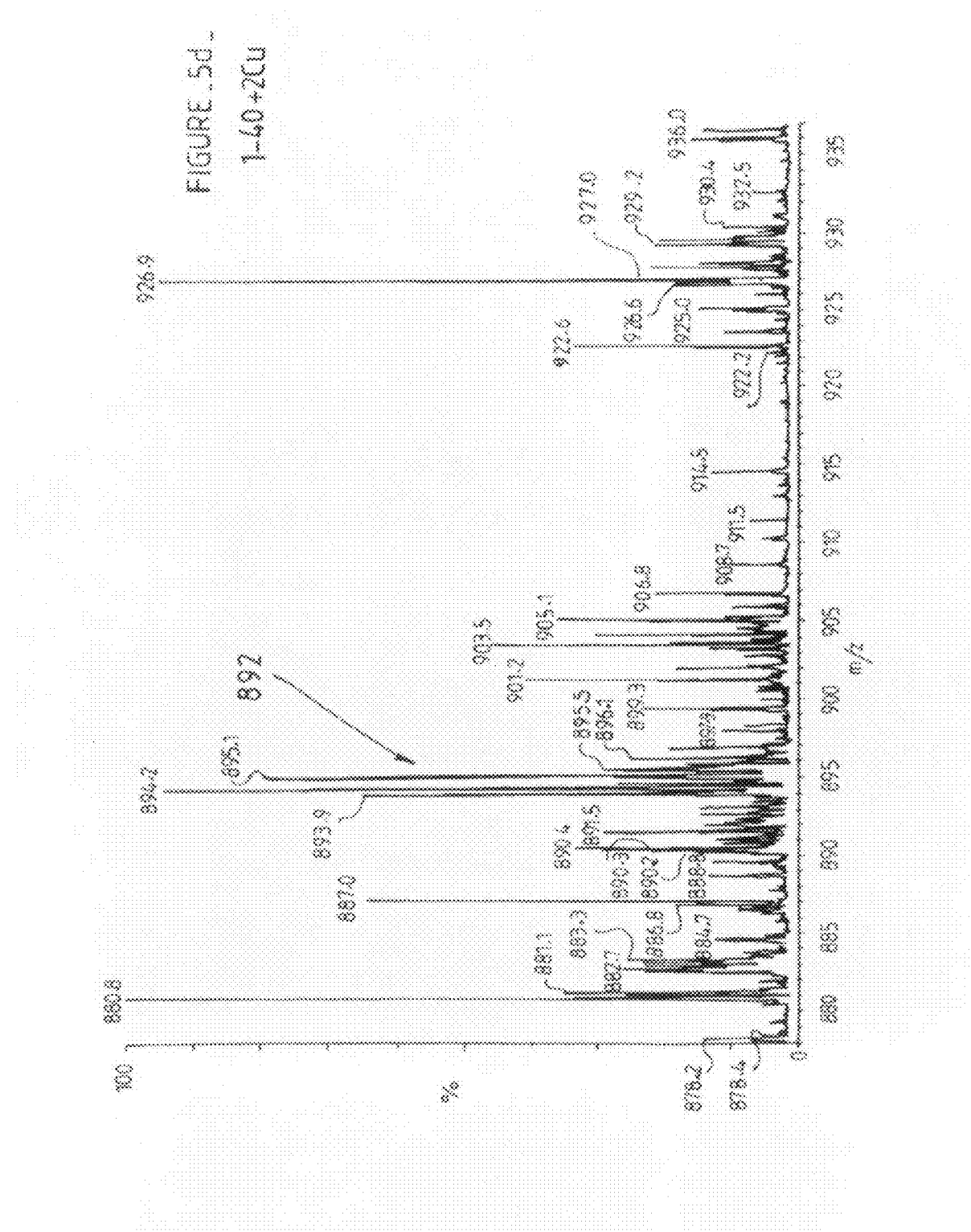

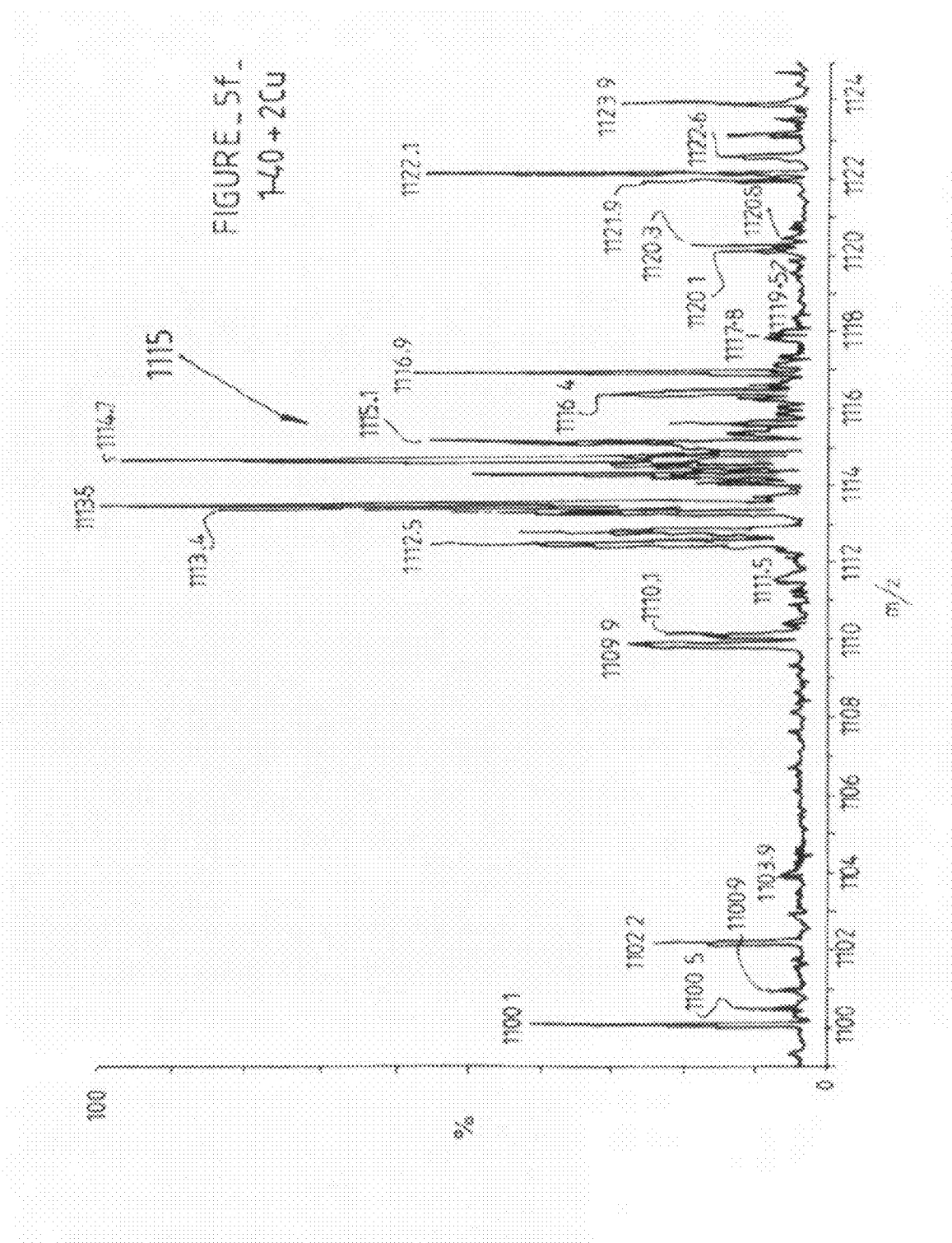

NEUROTOXIC OLIGOMERS

CROSS REFERENCE TO RELATED APPLICATIONS

This is application is a divisional of U.S. application Ser. No. 10/312,437, filed on Jun. 16, 2003, which is the national phase of PCT/AU01/00786 having an international filing date of Jun. 28, 2001, which claims priority from U.S. Provisional Application No. 60/214,779, filed on Jun. 28, 2000 and U.S. Provisional Application No. 60/242,177, filed on Oct. 23, 2000.

FIELD OF THE INVENTION

This invention relates to methods and compositions for the treatment or alleviation of Alzheimer's disease and of other conditions related to abnormal protein aggregation. In particular, the invention relates to methods and compositions for the immunotherapy of Alzheimer's disease, Parkinson's disease, and cataract.

BACKGROUND OF THE INVENTION

The characteristic amyloid lesions of Alzheimer's disease (AD) are primarily composed of Amyloid β (Aβ) (Glenner & Wong, 1984), a 39-43 amino acid protein which is a normally soluble protein found in biological fluids. Amyloid formation is linked to the pathogenesis of the disease, so identifying the neurochemical changes which lead to the inhibition of Aβ catabolism and its accumulation in the neocortex would be an important clue to the pathogenesis of AD.

Although the fundamental pathology, genetic susceptibility and biology associated with AD are becoming clearer, a rational chemical and structural basis for developing effective drugs to prevent or cure the disease remains elusive. While the genetics of AD indicate that the metabolism of Aβ is intimately associated with the pathogenesis of the disease as indicated above, drugs for the treatment of AD have so far focused on "cognition enhancers", which do not address the underlying disease processes. These drugs have met with only limited success.

The nature of the deranged neurochemical environment in AD can be partly deduced from the post-translational modifications of amyloid Aβ. Aβ extracted from biological systems normally migrates as an apparent ~4 kD monomer on sodium dodecyl sulfate-polyacrylamide gel electrophoresis (SDS-PAGE; (Shoji et al., 1992)); however, Aβ extracted from specimens of AD-affected post-mortem brain migrates on SDS-PAGE as SDS-, urea- and formic acid-resistant oligomers (Masters et al., 1985; Roher et al., 1996; Cherny et al., 1999).

Matrix-assisted laser desorption ionization-mass spectrometry (MALDI-MS) of these SDS-resistant oligomers extracted from neuritic plaque and vascular amyloid indicates the presence of covalently cross-linked dimeric and trimeric Aβ species (Roher et al., 1996).

Synthetic $A\beta_{1-40}$ and $A\beta_{1-42}$ normally migrate as apparent monomers on SDS-PAGE, but form apparent higher molecular weight species upon incubation (Burdick et al., 1992). This process is accelerated by exposure to oxidative systems (Dyrks et al., 1992; Atwood et al., 1997).

Tyrosine cross-linking has been proposed as a mechanism of Aβ oligomerization in vivo, since tyrosine residues in synthetic human Aβ can be cross-linked by peroxidase-catalyzed oxidation systems (Galeazzi et al., 1999). As Rat Aβ, unlike human Aβ, lacks a tyrosine residue (Atwood et al., 1997), it is therefore resistant to metal-catalyzed oxidative oligomerization, and this perhaps explains the rarity of amyloid deposits in these animals (Vaughan and Peters, 1981).

Tyrosine cross-linking in proteins is a sensitive marker of oxidative stress. Covalent carbon-carbon bridges or carbon-oxygen bridges are formed between single tyrosyl residues and/or dityrosyl residues, resulting in a number of stable, fluorescent reaction products (Gross and Sizer, 1959; Amado et al., 1984, Jacob et al., 1996). The major reaction products of the free tyrosyl radical are the intensely fluorescent amino acids 3,3'-dityrosine (DT), 3,3',3'-trityrosine (TT) and pulcherosine (P), and the non-fluorescent isodityrosine (iso-DT) (Gross and Sizer, 1959; Amado et al., 1984, Jacob et al., 1996; Heinecke et al., 1993). DT and 3-nitrotyrosine levels are elevated in the hippocampus and neocortical of brains of patients with AD compared to the same regions of normal brain, and are also elevated in ventricular cerebrospinal fluid in AD patients (Hensley et al., 1998).

Tyrosine cross-linking may also be important in other neurodegenerative diseases such as Parkinson's disease, and other conditions in which α-synuclein fibrils are deposited. These include Parkinson's disease itself, dementia with Lewy body formation, multiple system atrophy, Hallerboden-Spatz disease, and diffuse Lewy body disease. Exposure of recombinant α-synuclein to nitrating agents results in nitration of tyrosine residues as well as oxidation of tyrosine to form DT; this results in cross-linking of α-synuclein to form stable aggregates (Souza et al, 2000). The same authors also found that monoclonal antibodies raised against nitrated synuclein bound specifically to Lewy bodies and to glial cell inclusions in a variety of synucleinopathies (Duda et al., in preparation referred to in Souza et al., 2000).

We have now found that human amyloid-derived Aβ contains tyrosine cross-links, and includes both dityrosine and trityrosine cross-linked species. These cross-links can be replicated in vitro, for example by incubating synthetic human Aβ with peroxidase and $H_2O_2$, or with $H_2O_2$ in the presence of copper ions. These modifications are protease-resistant, and therefore we propose that tyrosine cross-linkage in AD caused by abnormal interaction of Aβ with $H_2O_2$ and peroxidases or copper ions contributes to the formation of neurotoxic Aβ oligomers, and to the deposition of Aβ. Immunization against low molecular weight tyrosine cross-linked compounds rather than with whole Aβ can therefore be used for treatment or prevention of AD, without the risk of provoking autoimmune complications which could otherwise be induced by immunization with intact Aβ or large fragments thereof. By restricting the target for immunotherapy to an abnormal fragment or portion of the molecule, it may be possible to minimise undesirable interference with the normal function of the molecule, while providing an active therapy against the abnormal molecule. It will be appreciated that either active or passive immunization may be used.

The oxidative processes which give rise to covalent cross-linking of proteins via tyrosine are also associated with other disorders which are characterised by pathological aggregation and accumulation of specific proteins. It is therefore considered that these conditions also will be amenable to prevention or treatment by the method of the invention.

It will be clearly understood that, although a number of prior art publications are referred to herein, this reference does not constitute an admission that any of these documents forms part of the common general knowledge in Australia or in any other country.

SUMMARY OF THE INVENTION

In a first aspect, the invention provides a method of prophylaxis, treatment or alleviation of a condition, in which the condition is characterised by pathological aggregation and accumulation of a specific protein associated with oxidative damage and formation of tyrosine cross-links, the method comprising the step of immunizing a subject in need thereof with an immunizing-effective dose of one or more compounds selected from the group consisting of dityrosine, trityrosine, tetratyrosine (also known as pulcherosine), oxidised tyrosine orthologues such as o-tyrosine and m-tyrosine, nitrotyrosine, and peptides comprising tyrosine cross-links, and optionally also comprising copper ions complexed to the compound. These compounds are collectively referred to herein as "tyrosine cross-linked compounds".

A person of ordinary skill in the art will recognise that an immunizing-effective dose of the compound is one which will elicit antibody which is able to bind to a tyrosine cross-linked compound. Such a person will also be able to determine whether a particular tyrosine cross-linked compound elicits an antibody.

In a preferred embodiment, the pathologically aggregated form of the specific protein comprises a tyrosine cross-linked moiety. In a particularly preferred embodiment, the tyrosine cross-linked compound is a peptide which is an immunogenic portion of the pathologically aggregated form of the specific protein, the peptide comprising a cross-linked tyrosine moiety linked to residues upstream and downstream of the cross-linked tyrosine.

In a preferred embodiment, the tyrosine cross-linked compound is a dityrosine cross-linked compound.

Up to 3 equivalents of copper per equivalent of dityrosine may be used, provided that each dose administered contains no more than 1 µM copper.

Optionally the compound used for immunisation is coupled to a carrier protein which is itself immunogenic, such as tetanus toxoid, keyhole limpet haemocyanin, or albumin. Also optionally the compound may be administered together with an adjuvant such as alum, monophosphoryl lipid, a muramyl peptide, an iscom such as QS21 and the like. Persons skilled in the art will be well aware of suitable carriers and adjuvants.

Where a peptide comprising tyrosine cross-links is used, this is preferably a minimal and immunogenic portion of the particular protein associated with the condition, which is constituted by the dityrosine moiety linked to residues upstream and downstream of the cross-linked tyrosine. Where the condition is Alzheimer's disease, preferably the peptide comprising tyrosine cross-links is derived from the sequence surrounding tyrosine 10 in the amino acid sequence of human $A\beta_{1-40}$ or $A\beta_{1-42}$.

In all aspects of the invention, where a peptide comprising tyrosine cross-links is used, it is preferred that the tyrosine cross-links are obtainable by oxidation in the presence of copper ions.

More preferably the peptide also comprises copper ions complexed to dityrosine.

Immunization may be administered by any convenient route, including subcutaneous, intramuscular or intravenous injection, application to mucosal surfaces, or topical administration, for example in an ointment.

The dose of the compound to be administered will vary, depending on the nature of the individual compound, the weight, age and general state of health of the patient, and whether an adjuvant is used. It is contemplated that the dose will be in the region of 0.1 µg to 200 mg of DT, more preferably 1 to 50 mg, most preferably 10 to 20 mg. Although a single immunization may be given, preferably multiple immunizations are administered, for example once a week for one to twelve months, more preferably for four months. A booster series may be given after six to twelve months. The immune response is monitored by measuring DT antibodies; any convenient assay system may be used, such as ELISA.

In an optional embodiment, the method also comprises the additional steps of identifying the predominant forms of the tyrosine cross-links in the pathologically aggregated specific protein; and synthesising one or more tyrosine cross-linked compounds comprising one or more of the predominant forms of tyrosine cross-links.

In an alternative form of this aspect of the invention, the immunization may be passive. Thus the invention provides a method of a method of prophylaxis, treatment or alleviation of a condition, in which the condition is characterised by pathological aggregation and accumulation of a specific protein associated with oxidative damage and where the pathologically aggregated form of the specific protein comprises a tyrosine cross-link, the method comprising the step of administering an effective amount of an antibody or an antibody fragment, said antibody or antibody fragment is raised against a tyrosine cross-linked compound, said compound being an immunogenic portion of the pathologically aggregated form of the specific protein and comprising a tyrosine cross-link, and which antibody or antibody fragment is capable of specifically binding the pathologically aggregated form of the specific protein, to a subject in need of such treatment.

The antibody may be polyclonal or monoclonal. Where the antibody is polyclonal, it is preferably of human origin, and may for example be derived from pooled human serum from normal healthy individuals. Alternatively serum from individuals who have been hyperimmunized against a tyrosine cross-linked compound may be used. Protocols for hyperimmunization are known in the art. The antibody may be isolated from serum by any convenient method; a variety of suitable methods is known in the art. Where the antibody is monoclonal, it is preferably humanized. It will be clearly understood that antigen-binding fragments of antibodies, such as F(ab'), F(ab')$_2$, FV or monoclonal scFv, are within the scope of the invention. Methods for production and purification of polyclonal and monoclonal antibodies and for recombinant production of humanized monoclonal antibodies or of scFv fragments are well known in the art. See for example Harlow and Lane (1988); WO90/07861; and WO92/01047. Humanized monoclonal antibodies may also be produced in transgenic mammals; see for example WO91/10741 and WO93/12227.

It is preferred that the antibody reacts specifically with the pathologically aggregated form of the specific protein, and does not react significantly with the unaggregated form of the protein.

Following either active or passive immunization, the patient is monitored for clinical improvement, which may commence within as little as one week, but more probably may be observed at six weeks, and may take as long as 12 months. The normal clinical indices which are used in the monitoring of patients with the relevant condition are used. The attending clinician will be aware of the most suitable tests to use.

Where the treatment is prophylactic, the patient is monitored for signs of development of the condition. The patient may be at risk as a result of genetic linkage, e.g. in familial Alzheimer's disease or Huntington's disease.

In a second aspect, therefore, the invention provides a prophylactic or therapeutic composition for use in the method of the invention, comprising a tyrosine cross-linked compound, together with a pharmaceutically acceptable carrier, and optionally further comprising an adjuvant, and/or copper ions complexed to the compound.

In an alternative embodiment of the second aspect, the invention provides a prophylactic or therapeutic composition for use in the passive immunization method of the invention, comprising an antibody directed against a tyrosine cross-linked compound as defined above, or a fragment thereof which is capable of binding to the tyrosine cross-linked compound, together with a pharmaceutically acceptable carrier.

In a third aspect, the invention provides a method of diagnosis of a condition, in which the condition is characterised by pathological aggregation and accumulation of a specific protein associated with oxidative damage and formation of tyrosine cross-links, the method comprising the step of assaying a sample of a biological fluid from a subject suspected of suffering from the condition for the presence of a compound selected from the group consisting of dityrosine, trityrosine, tetratyrosine, oxidised tyrosine orthologues such as o-tyrosine and m-tyrosine, nitrotyrosine, and peptides comprising tyrosine cross-links.

In an alternative aspect, the method comprises the step of assaying a biological fluid from a subject suspected of suffering from the condition for the presence of antibody directed against a tyrosine cross-linked compound.

Preferably the biological fluid is selected from the group consisting of blood, plasma, serum, cerebrospinal fluid, urine, and saliva. Preferably the compound is dityrosine.

The assay may be performed by any suitable means, but is most conveniently performed by an ELISA assay using antibody directed against tyrosine cross-linked compounds. Such an assay may conversely be used to detect antibody directed against a tyrosine cross-linked compound. Preferably the antibody is a monoclonal antibody, or a mixture of monoclonal antibodies. Alternatively the assay may be performed by measuring fluorescence at an excitation wavelength of 325 nm and an emission wavelength of 350-500 mm.

In all three aspects of this invention, preferably the condition is selected from the group consisting of Alzheimer's disease, amyotrophic lateral sclerosis, motoneuron disease, cataract, Parkinson's disease, Creutzfeldt-Jacob disease, Huntington's disease, dementia with Lewy body formation, multiple system atrophy, Hallerboden-Spatz disease, and diffuse Lewy body disease, or cataract.

More preferably the condition is Alzheimer's disease or Parkinson's disease.

For the purposes of this specification it will be clearly understood that the word "comprising" means "including but not limited to", and that the word "comprises" has a corresponding meaning.

(A) fluorescent spectra ($\lambda_{ex}$ 325, $\lambda_{em}$ 350-500);

(B) migration on SDS-PAGE (by Western blot using 4G8);

(C) $A\beta_{1-42}$ (10 nM) was incubated with $H_2O_2$ (1 µM) and peroxidase (7.5 µg/ml) for 5 days at 37° C. in phosphate buffered saline, pH 7.4. The product (lane 2) was compared to peptide incubated under the same conditions in the absence of $H_2O_2$/peroxidase (lane 1) by SDS PAGE and Western blot (4G8)

Figure 2A:
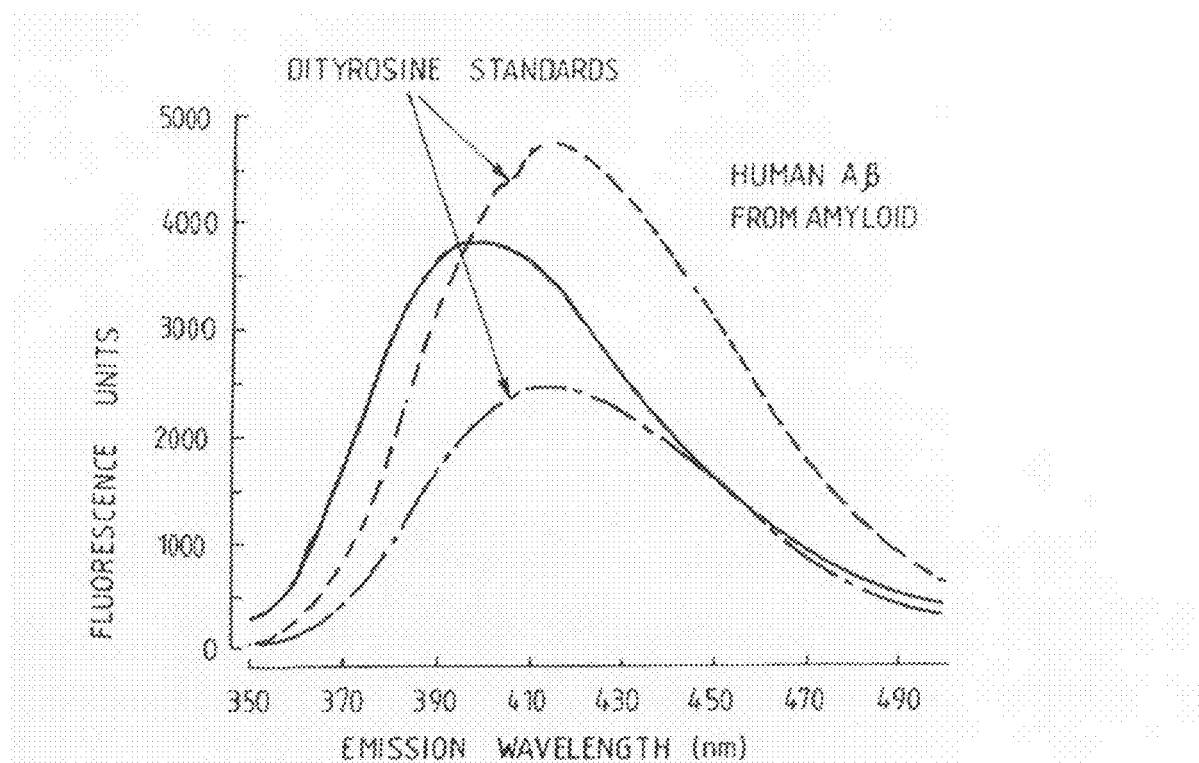
Figure 2B:
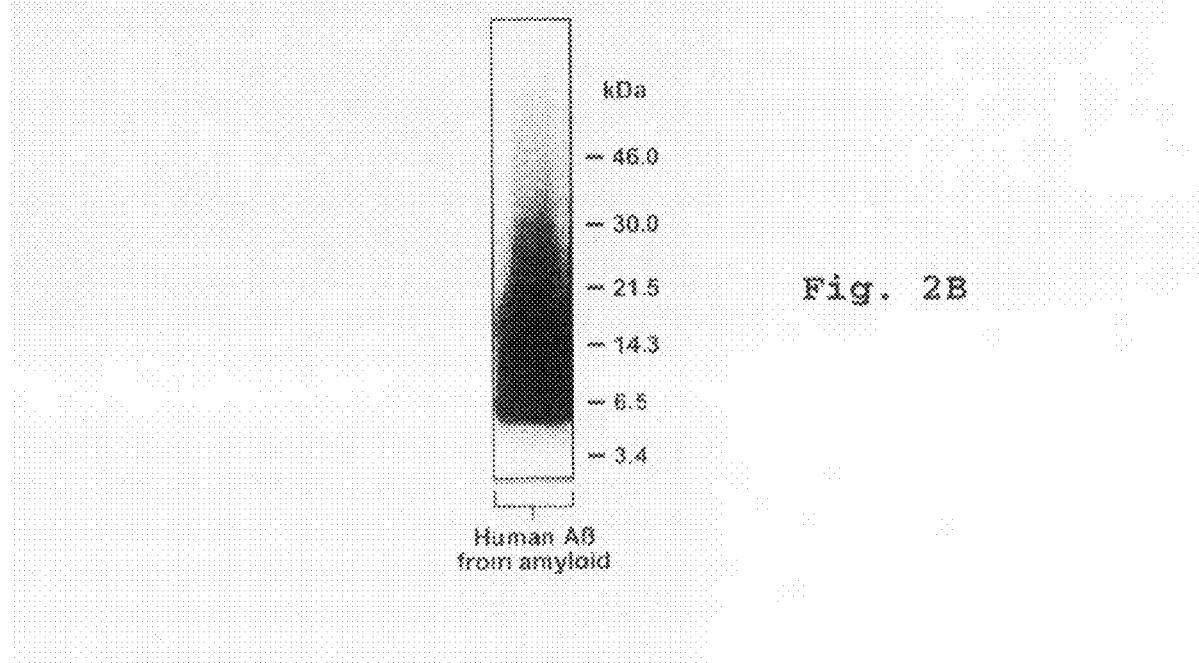

FIG. 2 shows that human amyloid-derived Aβ contains tyrosine cross-linked oligomers. Human amyloid-derived Aβ (20 µM) (Roher et al., 1996) was analysed by fluorescence spectroscopy compared to a pure DT standard ($\lambda_{ex}$ 325, $\lambda_{em}$ 350-500) (A), and Western blot (4G8) (B).

Figure 3A:
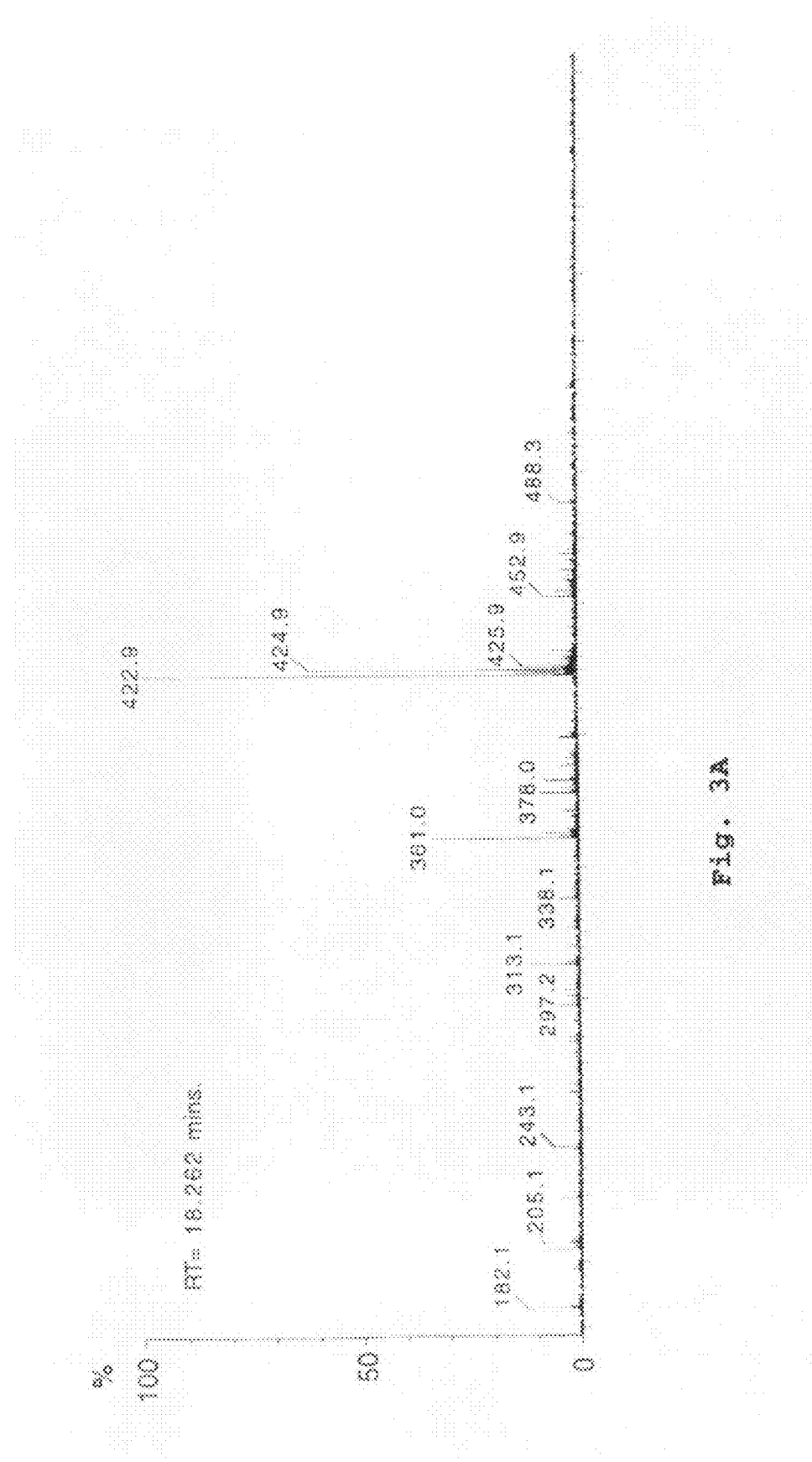
Figure 3B:
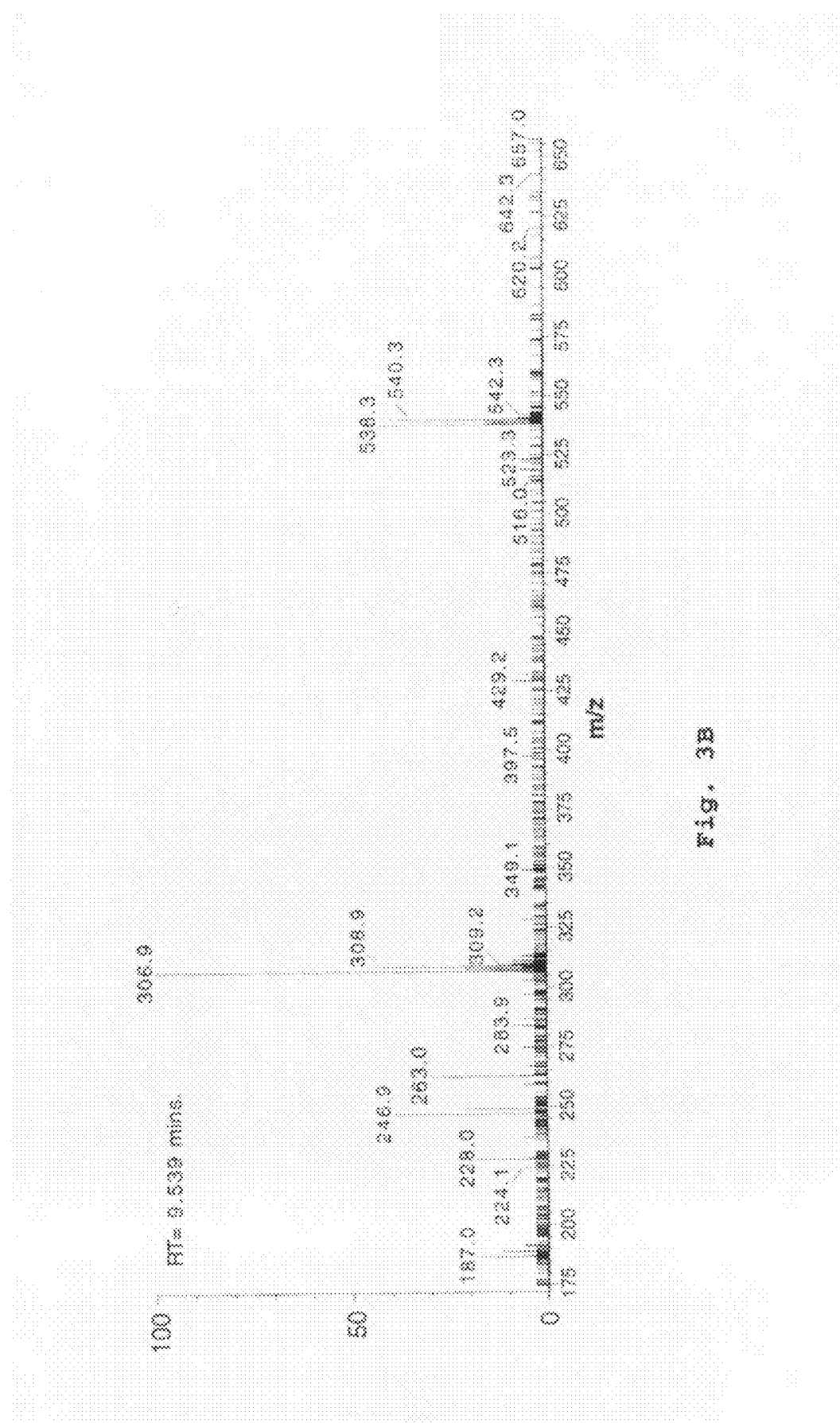

FIG. 3 shows that dityrosine and trityrosine cross-links are present in human amyloid-derived Aβ, and that they bind copper.

(A) and (B) Human amyloid was purified, hydrolyzed and the mass spectrum determined after chromatographic separation. Two individual scans reflecting analyses of the same sample eluting at different chromatographic retention times (RT) are shown.

(C) Absorbances at 280 nm and 315 nm of purified DT in the presence of increasing concentrations of $CuSO_4$ or NaCl.

Figure 4A:
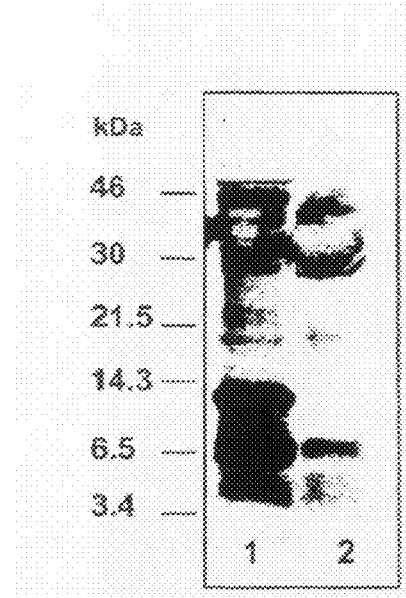

FIG. 4 shows that soluble human Aβ binds copper with high affinity.

(A) silver stain of crude soluble extract (1) and pH 1 eluate from the copper-chelating Sepharose column (2).

(B) Western blot of pH 1 eluate probed with WO2, G211 and G210.

Figures 1, 5E, 42:
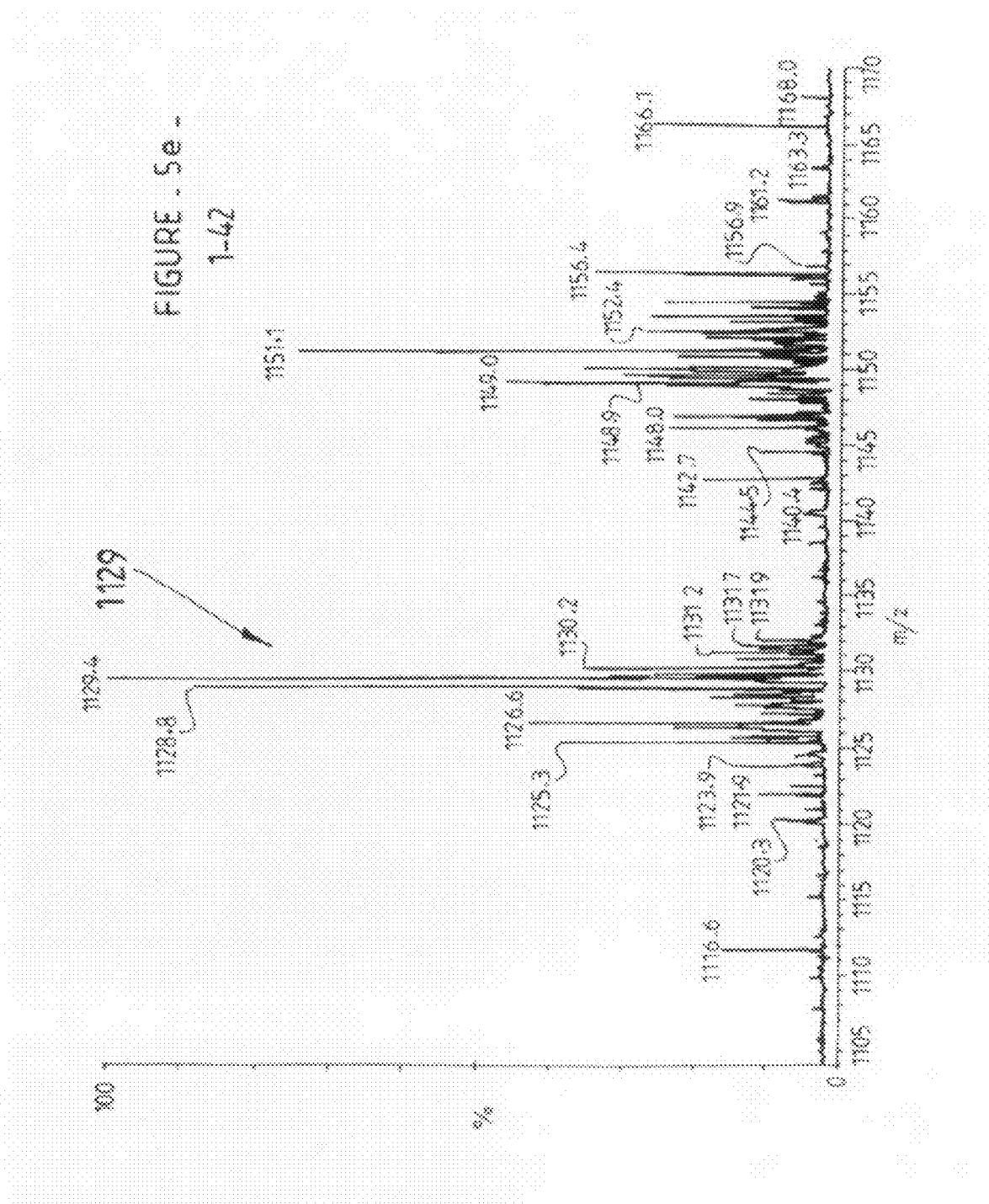

FIG. 5 shows the results of LC-MS analysis, confirming that human Aβ binds copper.

LC-MS analysis of crude (5A) and IMAC purified (5B) soluble extracts.

Mass spectra of $A\beta_{1-42}$ (5C) and (5E), and $A\beta_{1-40}$ with two bound copper atoms (5D) and (5F).

The IMAC and LC-MS data demonstrate that brains derived Aβ can bind copper.

Figure 6A:
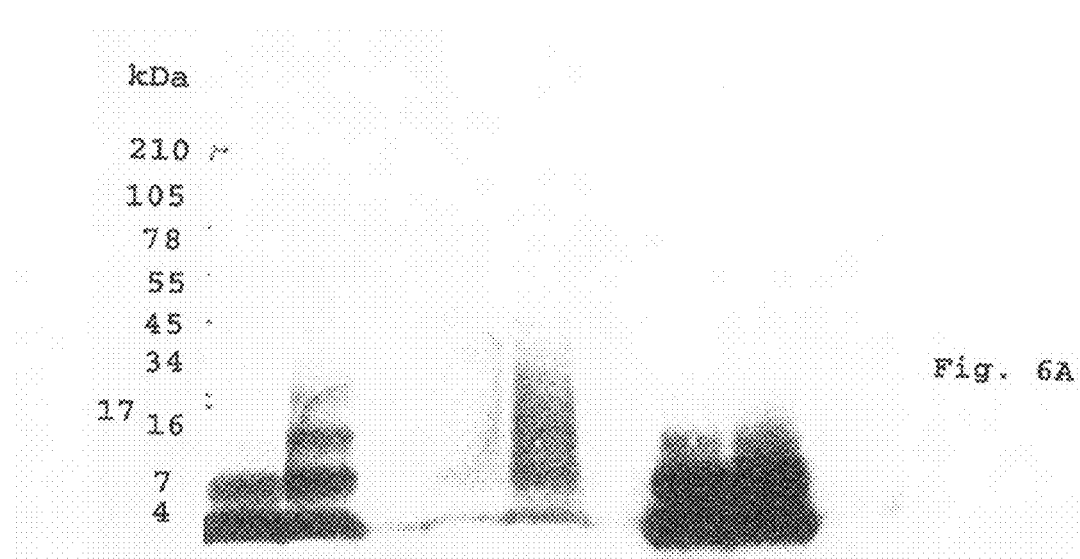
Figure 6B:
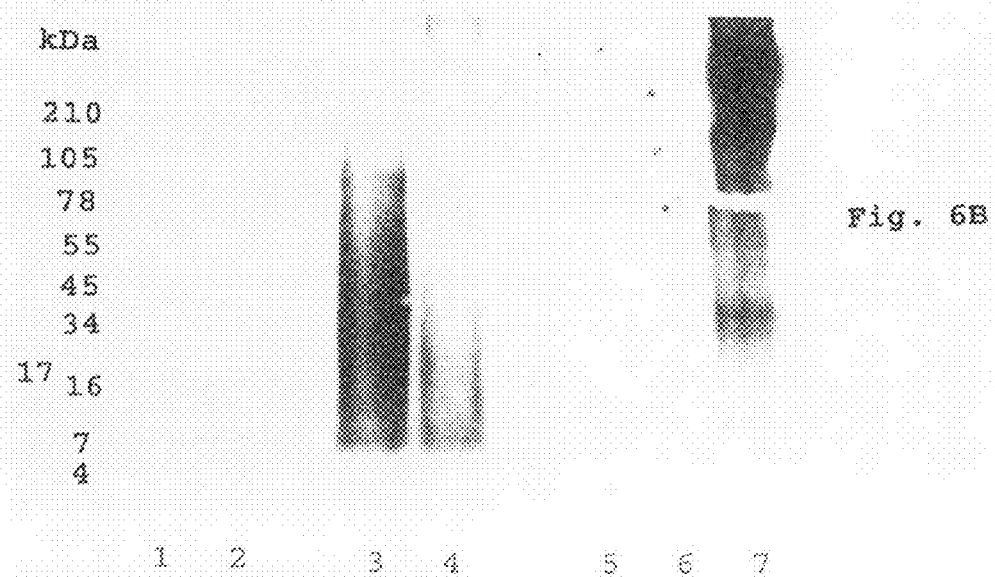
Figure 7A:
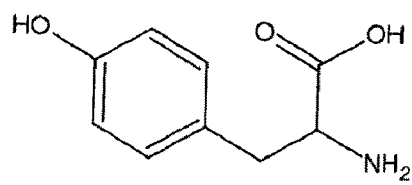
Figure 7B:
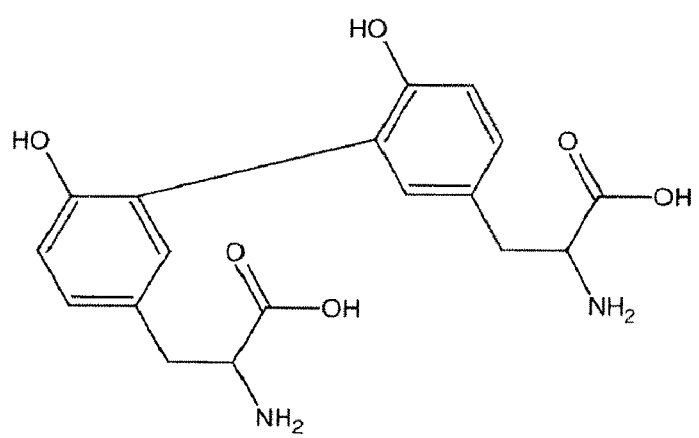
Figure 7C:
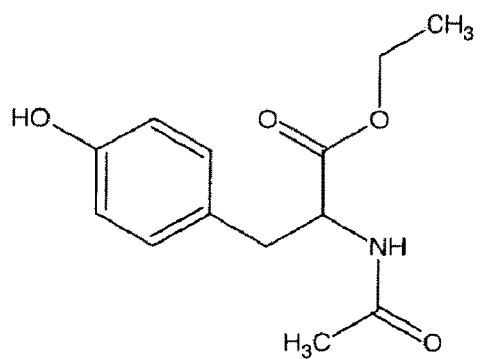
Figure 7D:
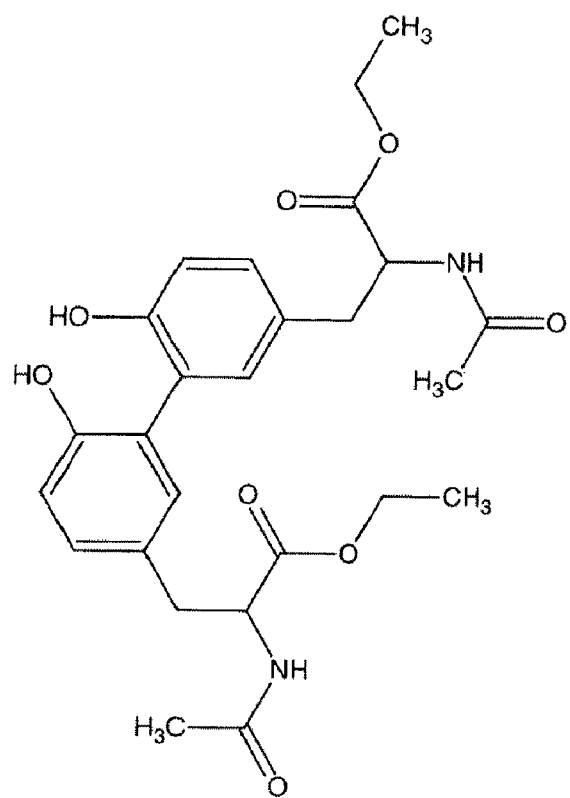
Figure 7E:
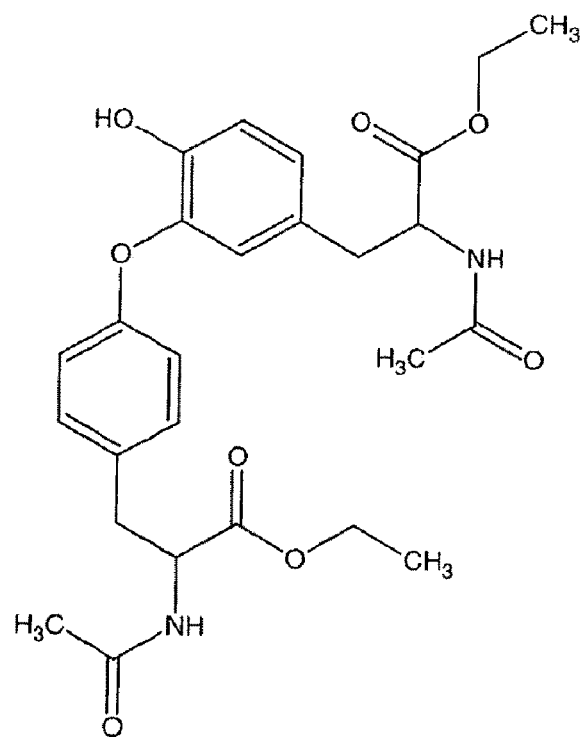
Figure 7F:
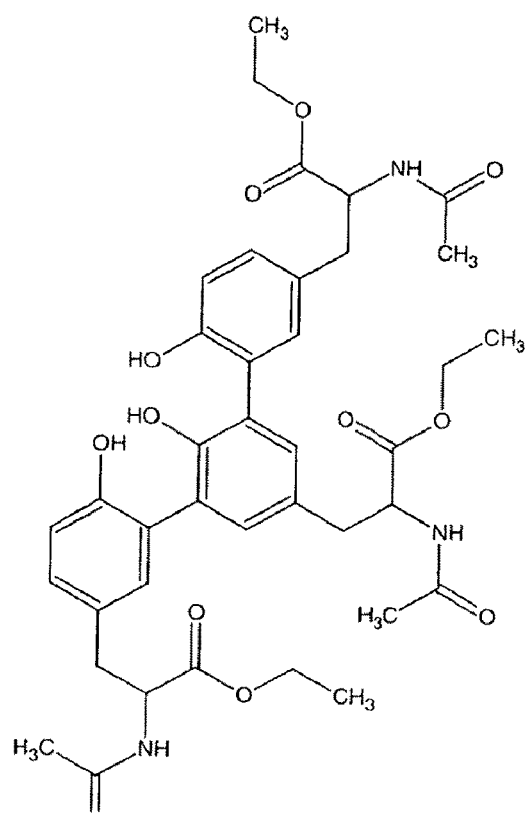
Figure 7G:
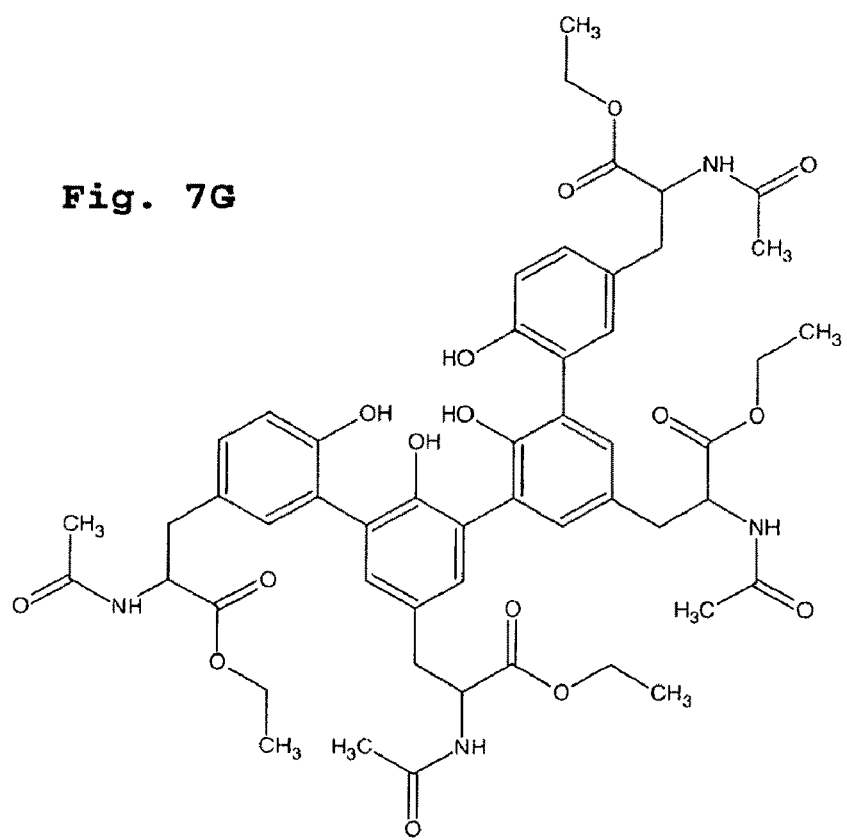
Figure 7H:
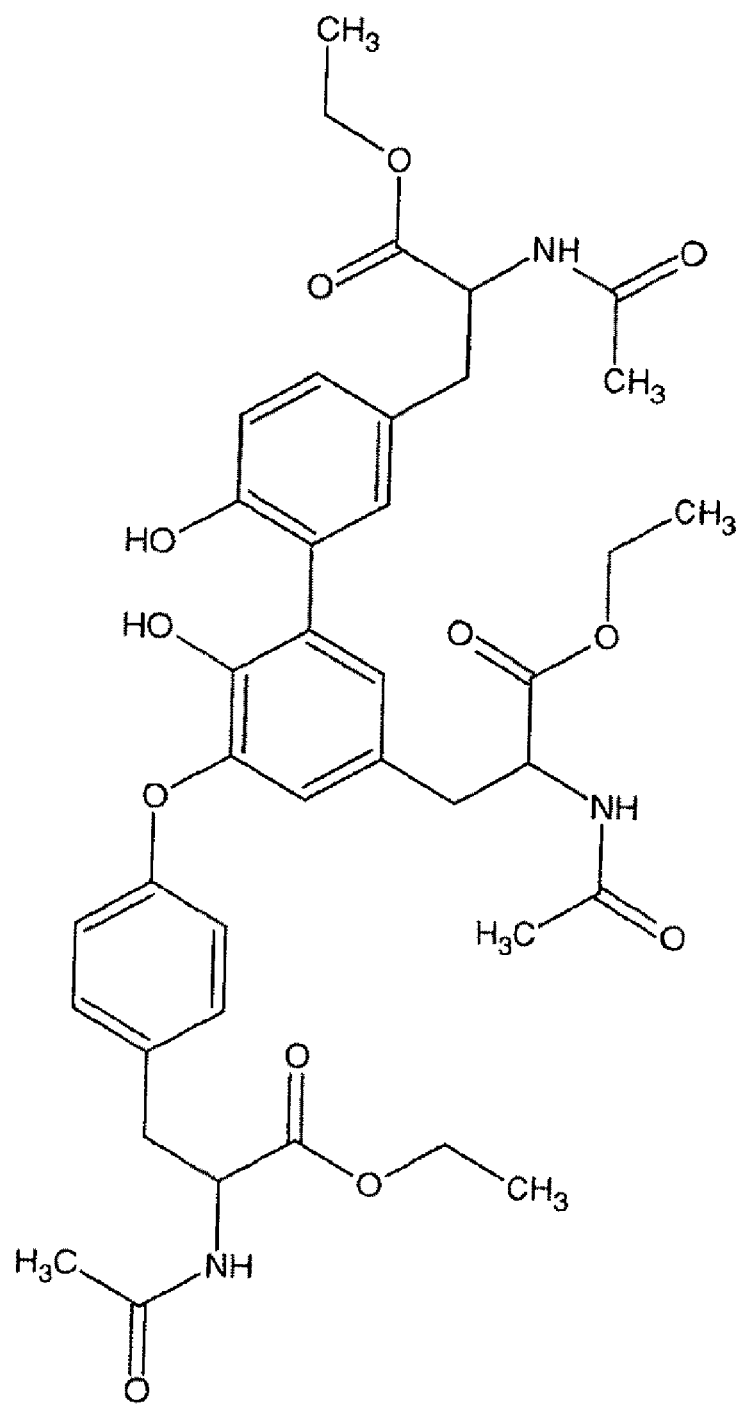

FIG. 6 shows the detection of dityrosine in cross-linked $A\beta_{1-40}$ and $A\beta_{1-42}$ in Western blots.

Two techniques to create the dityrosine linkages are also compared.

The top-Western blot (A) demonstrates the presence of Aβ using the WO2 antibody. The bottom blot (B) demonstrates the presence of dityrosine linkages recognised by the monoclonal antibody IC3. This antibody was raised against a form of dityrosine prepared using borate/$H_2O_2$/horseradish peroxidase.

Lane 1 $A\beta_{1-40}$—borate cross linking
Lane 2 $A\beta_{1-42}$—borate cross linking
Lane 3 $A\beta_{1-40}$—copper cross linking
Lane 4 $A\beta_{1-42}$—copper cross linking
Lane 5 $A\beta_{1-40}$—untreated
Lane 6 $A\beta_{1-42}$—untreated
Lane 7 Dityrosine conjugated to KLH FIG. 7 shows examples of the forms of tyrosine cross-links produced as potential immunogens. These structures contain tyrosine cross-links and have the carboxy- and amino-termini acetylated to mimic the presence of additional amino acid residues that would normally be present on either side of a tyrosine cross-linked moiety in a tyrosine cross-linked peptide. The presentation of multiple copies of the dityrosine antigen is designed to improve the strength of the immune response generated.

7A Tyrosine
7B Dityrosine
7C Atee
7D DiAtee
7E IsoDiAtee
7F TriAtee
7G Tetraktee.
7H Alternate form of TriAtee with one iso bond.

Figure 8A:
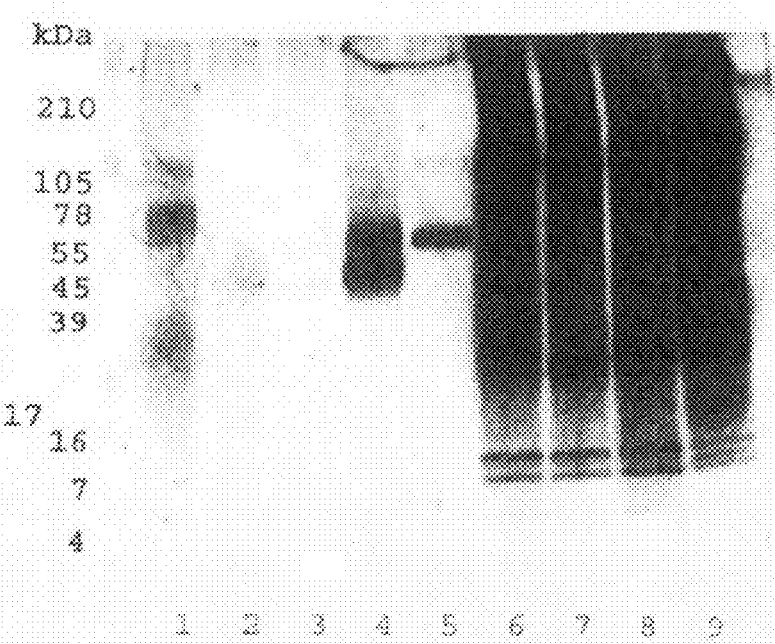
Figure 8B:
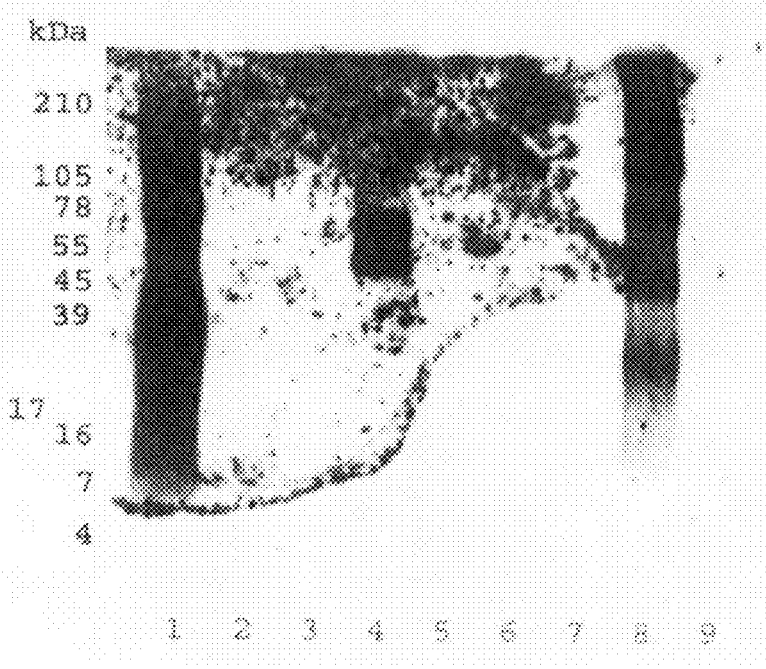

FIG. 8 shows the detection of dityrosine bonds in a variety of tyrosine cross-linked species in Western Blots. The DT-containing species include dityrosine cross-linked $A\beta_{9-16}$ dimer or trimer linked to BSA, and various poly-DT species linked to either BSA or KLH carrier proteins. The top Western blot (A) demonstrates the ability of the sample to bind to a polyclonal rabbit antiserum raised against DT which was prepared using the borate/$H_2O_2$/peroxidase technique and linked to KLH using glutaraldehyde (discussed in Example 7). The bottom Western blot (B) demonstrates the presence of dityrosine linkages recognised by the monoclonal antibody IC3. This antibody was raised against a form of dityrosine also prepared using the borate/$H_2O_2$/peroxidase technique.

Lane 1 Abeta 9-16 DT dimer BSA
Lane 2 Abeta 9-16 DT trimer—BSA
Lane 3 Crude ATEE—BSA
Lane 4 PolyTyr—BSA
Lane 5 BSA
Lane 6 Abeta trimer—KLSH
Lane 7 Crude ATEE—KLH
Lane 8 PolyTyr—KLH
Lane 9 KLH

DETAILED DESCRIPTION OF THE INVENTION

The invention will now be described in detail by way of reference only to the following non-limiting examples and drawings.

Abbreviations used herein are as follows:

| | |
|---|---|
| AD | Alzheimer's disease |
| DT | 3,3'-dityrosine |
| TT | 3,3'3'-trityrosine |
| P | pulcherosine |
| iso-DT | isodityrosine |

EXPERIMENTAL PROCEDURES

Reagents and Aβ Peptide Preparation

Oligomeric Aβ was extracted from amyloid plaques of human AD-affected brains as previously described (Roher et al., 1996). The purified amyloid Aβ was solubilized in formic acid, and then immediately dialyzed with 5 changes of 100 mM ammonium bicarbonate, pH 7.5 before use.

Human $Aβ_{1-40}$, $Aβ_{1-42}$ and rat $Aβ_{1-40}$ were synthesized, purified and characterized by HPLC analysis, amino acid analysis and mass spectroscopy by W. M. Keck Foundation Biotechnology Resource Laboratory (Yale University, New Haven, Conn.), and corroborative studies were performed using peptide synthesized by Quality Control Biochemicals, Inc. (Hopkinton, Mass.).

Each peptide was identified as a single peak by HPLC. Synthetic Aβ peptides were dissolved in doubly deionized water at a concentration of 0.5-1.0 mg/ml, sonicated for 3 main and then centrifuged for 20 min. at 10 000 g and the supernatant (stock Aβ) used on the day of the experiment. The concentrations of stock Aβ peptides were determined by spectrophotometric absorbance at 214 nm or by Micro BCA protein assay (Pierce, Rockford, Ill.) as previously described (Atwood et al., 1998).

Prior to use, all buffers and stock solutions of metal ions were filtered though a 0.22 µm filter (Gelman Sciences, Ann Arbor, Mich.) to remove particulate matter. All other reagents were analytical grade or purer. Horseradish peroxidase was obtained from Sigma Chemical Co. (St. Louis, Mo.).

Preparation and Fluorescence Analysis of Dityrosine and Tyrosine Cross-Linked Aβ

DT standards were generated by incubating L-tyrosine (1 mg/ml) solubilized in borate buffer (50 mM, pH 9.5) with $H_2O_2$ (5 mM) and horseradish peroxidase (7.5 µg/ml) for 1 day at 37° C. (Amado et al., 1984).

Cross-linked Aβ was generated by incubating Aβ (50 µM) in borate buffer (50 mM, pH 9.5) and with $H_2O_2$ (1 mM) and peroxidase (7.5 µg/ml) for 5 days at 37° C. In a separate experiment to study this reaction under conditions which approached physiological, $Aβ_{1-42}$ was diluted to 10 nM in phosphate-buffered saline (PBS, pH 7.4), and incubated with 1 µM $H_2O_2$ and peroxidase (7.5 µg/ml) for 5 days at 37° C. Following the incubation, the samples were lyophilized to bring the peptide into a concentration range which could be detected by Western blot (see below).

Reaction products were separated by fast phase liquid chromatography (FPLC). Excess borate was first precipitated from samples prior to chromatography by centrifugation at 0° C. Samples were then acidified by addition of 0.25% TFA and remaining insoluble material removed by filtration (0.22 µm pore size). Samples were loaded on to a 3 ml Resource RPC column (Pharmacia, Uppsala, Sweden) and the column washed with water containing 0.1% TFA. Bound species were eluted with a 0-100% linear gradient of acetonitrile containing 0.1% TFA at 1 ml/min over 45 min and collected in 0.5 ml fractions. Fractions were dried, reconstituted in water and assayed for dityrosine by fluorescence (excitation 330 nm; emission 400 nm) and WV absorbance (284 nm)). Peak fractions were further characterized by mass spectrometry, and dityrosine quantitated using the extinction coefficient ($E_{315}$ nm=8380 $M^{-1}$ $cm^{-1}$; Malencik et al., 1996).

Solutions were analyzed for the presence of fluorescent compounds using a Hitachi F-4500 spectrofluorometer. DT, TT and P have characteristic emission spectra ($λ_{ex}$ 325 nm, $λ_{em}$ 350-500 nm), which are quite distinct from those of tyrosine and tryptophan, which do not fluoresce at these wavelengths. There was a linear increase in fluorescence at this emission range with increasing dityrosine concentration between 0-50 µM.

MALDI-TOF Mass Spectrometry

Samples of SDS-resistant, oligomeric, human amyloid-derived Aβ were hydrolyzed in vacuo with 6N HCl for 48 h at 105° C. Following this, samples were analyzed by liquid chromatography MALDI-TOF mass spectrometry (LC-MS) at the Harvard University Mass Spectrometry Facility.

Mass spectra were obtained using a LCT mass spectrometer (Micromass Inc, Beverly Mass.) interfaced with a HP 1100 liquid chromatograph, attached to a C18 reversed-phase column (2.1 mm×250 mm). LC-MS was performed using a gradient of buffer A (water—0.1% formic acid (FA)), and buffer B (acetonitrile—0.1% FA). The gradient was from 2% B (0-2 min), to 100% B (20-23 min).

Western Blot Analysis

Aliquots of each reaction (2 ng peptide) were collected into 15 µl sample buffer (containing 4% SDS, 5% β-mercaptoethanol) and heated to 95° C. (5 min). Samples were run on PAGE (Tricine gels, 10-20%; Novex, San Diego, Calif.), transferred to PVDF membranes (Bio-Rad Laboratories, Hercules, Calif.), fixed with glutaraldehyde (1%, v/v), blocked with milk (10%, w/v) and then probed with the anti-Aβ monoclonal antibody 4G8 (Senetek, Maryland Heights, Mich.) overnight at 4° C. In one experiment the monoclonal antibodies WO2 (epitope:residues 5-8), G211 (epitope:residues 35-42) or G210 (epitope:residues 33-40) were used. The blot was then incubated with anti-mouse horseradish peroxidase (HRP) conjugate (Pierce, Rockford, Ill.) for 2 h at room temperature, and developed with ECL reagent (Amersham, Little Chalfont, UK) or Supersignal Ultra (Pierce, Rockford, Ill.). The chemiluminescent signal was captured using the Fluoro-S Image Analysis System (Bio-Rad, Hercules, Calif.) and electronic images analyzed using Multi-Analyst Software (Bio-Rad, Hercules, Calif.). Molecular size markers were from Amersham (Arlington Heights, Ill.).

EXAMPLE 1

Figure 1A:
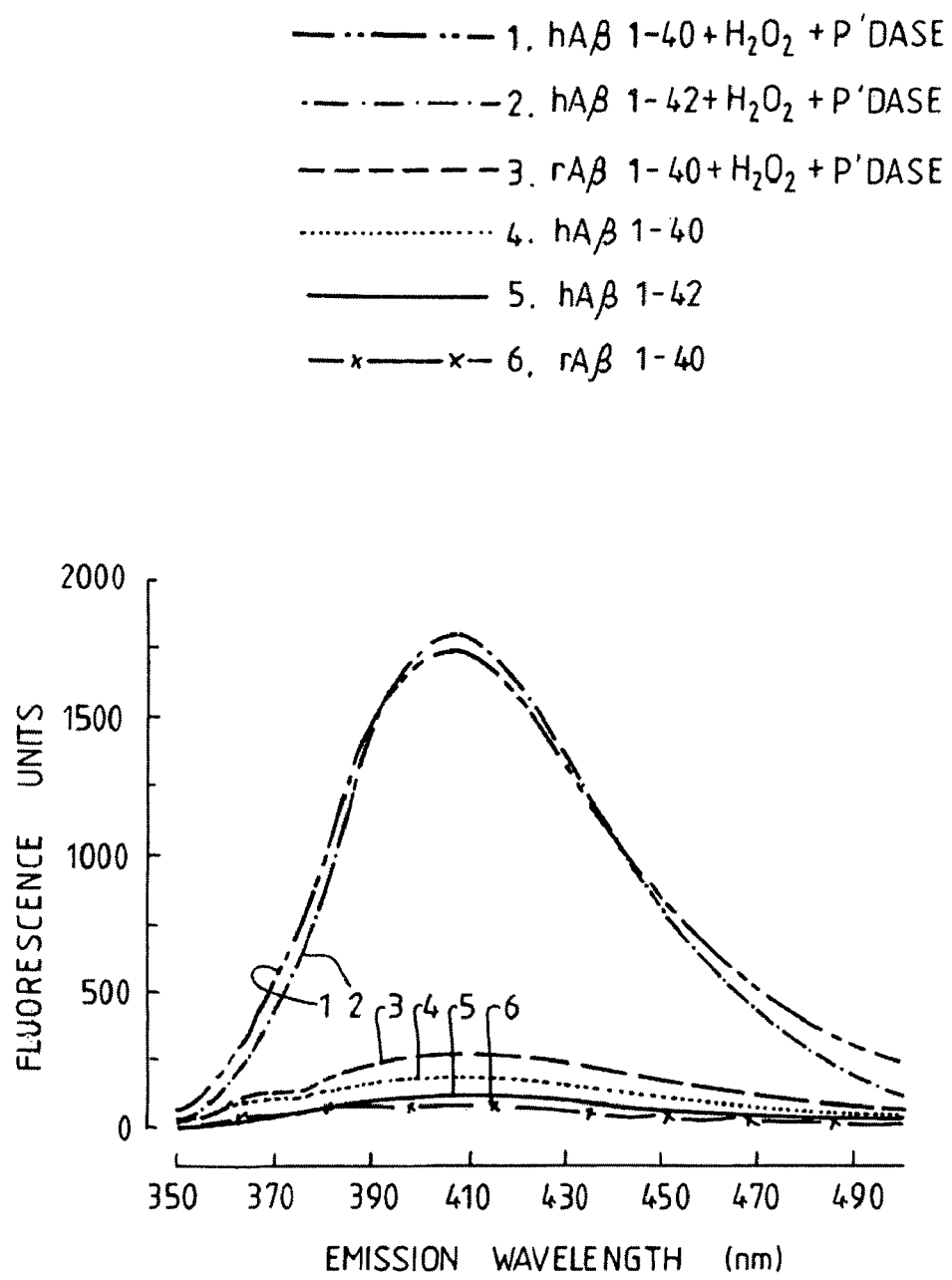
FIG. 1 shows that human Aβ, but not rat Aβ, develops fluorescence and SDS-resistance following peroxidase-catalyzed oxidation. Human $A\beta_{1-40}$, human $A\beta_{1-42}$, or rat $A\beta_{1-40}$ (50 µM) was incubated in 50 mM borate, pH 9.5±$H_2O_2$(1 mM) and peroxidase (7.5 µg/ml), for 1 day at 37° C.

Peroxidase-Catalyzed Aβ Polymerization is Accompanied by Formation of Tyrosine Cross-Links We initially tested whether peroxidase-catalyzed oxidative conditions could promote Aβ polymerization by measuring the fluorescence of human $Aβ_{1-40}$, human $Aβ_{1-42}$, and rat $Aβ_{1-40}$ (50 μM) incubated with or without $H_2O_2$ and peroxidase for 1 day. Fluorometric analysis of these samples indicated a marked increase in fluorescence in samples containing $Aβ_{1-40}$ and $Aβ_{1-42}$, as illustrated in FIG. 1A. These results are similar to those previously reported for synthetic human Aβ, achieved at a much higher peptide concentration, 1.25 mM (Galeazzi et al., 1999). In contrast to the behaviour of the human-sequence Aβ peptide, no increase in the fluorescence signal of rat $Aβ_{1-40}$ was observed after incubation with $H_2O_2$ and peroxidase, as also shown in FIG. 1A. This suggested that the fluorescent signal was specific for tyrosine oxidation products of Aβ, since rat Aβ lacks tyrosine (Shivers et al., 1988).

To confirm that these reactions resulted in Aβ polymerization, $Aβ_{1-40}$ and $Aβ_{1-42}$ treated as described above were run on SDS-PAGE and analyzed by Western blot. Both human synthetic $Aβ_{1-40}$ and $Aβ_{1-42}$ incubated with $H_2O_2$ and peroxidase displayed marked increases in apparent SDS-resistant polymers compared to untreated Aβ, as shown in FIG. 1B. Neither polymerization nor increased fluorescence was observed when Aβ was incubated with either $H_2O_2$ or peroxidase alone.

EXAMPLE 2

Polymerization Occurs Under Physiological Conditions

To determine whether $H_2O_2$/peroxidase-induced polymerization of synthetic Aβ occurs under conditions which approached physiological, we also incubated $Aβ_{1-42}$ at 10 mM with $H_2O_2$ at 1 μM and peroxidase (7.5 μg/ml) in PBS at pH 7.4. We observed that SDS-resistance of the peptide was again induced, as shown in FIG. 1C; however, oligomers of lower apparent molecular weight than those generated by using higher concentrations of substrates were generated, as illustrated in FIG. 13. The migration on SDS-PAGE of the apparent Aβ polymers under these conditions suggested the formation of dimers (8 Kd), trimers (13 kD) and tetramers (17 kD).

As shown in FIG. 2A and FIG. 23 respectively, fluorescent analysis of Aβ purified from AD-affected post-mortem brain tissue revealed the characteristic spectrofluorometric pattern of tyrosine cross-linked species; this purified protein migrated as apparent oligomers on SDS-PAGE, as previously described (Roher et al., 1996).

EXAMPLE 3

Tyrosine Cross-Linking of Oligomers

To confirm that the apparently oligomeric human amyloid-derived Aβ was tyrosine cross-linked, a sample was hydrolyzed and then analyzed by MALDITOF-MS. This analysis, illustrated in FIG. 3A, indicated a peak corresponding to 361 Da (m/z 361, representative of M+H), thereby confirming the existence of DT or iso-DT in the sample. A smaller peak corresponding to 540 Da was also detected, consistent with the presence of TT or P. Other prominent peaks were detected at 247, 263, 307, 309 and 538 Da; these may represent other modifications to Aβ amino acids, such as carbonylation (At-wood, 1999) and other amino acid cross-links.

More abundant fragments from the hydrolysis of human Aβ were also detected at 423 and 425 Da (ratio 3:2), suggestive of Cu binding to DT or iso-DT (Cu mass=63 & 65 Da, ≈ 2:1 natural isotope abundance).

EXAMPLE 4

Binding of Copper by Dityrosine

In order to test whether the peaks at 423 and 425 could be due to DT binding to Cu, we examined the interaction of $Cu^{2+}$ with DT by spectroscopic analysis, Dityrosine (50 μM) was solubilized in phosphate buffer (50 mM, pH 7.4) and the absorbance spectra (200-1000 nm) measured on a SPECTRAmax Plus (Molecular Devices). A trough (280 nm) and peak (315 nm) were apparent. Dityrosine was then incubated with increasing concentrations of $CuNO_3$ (0-200 μM) or NaCl (0-200 μM), and changes in absorbance at both 280 nm and 315 nm were monitored.

Figure 3C:
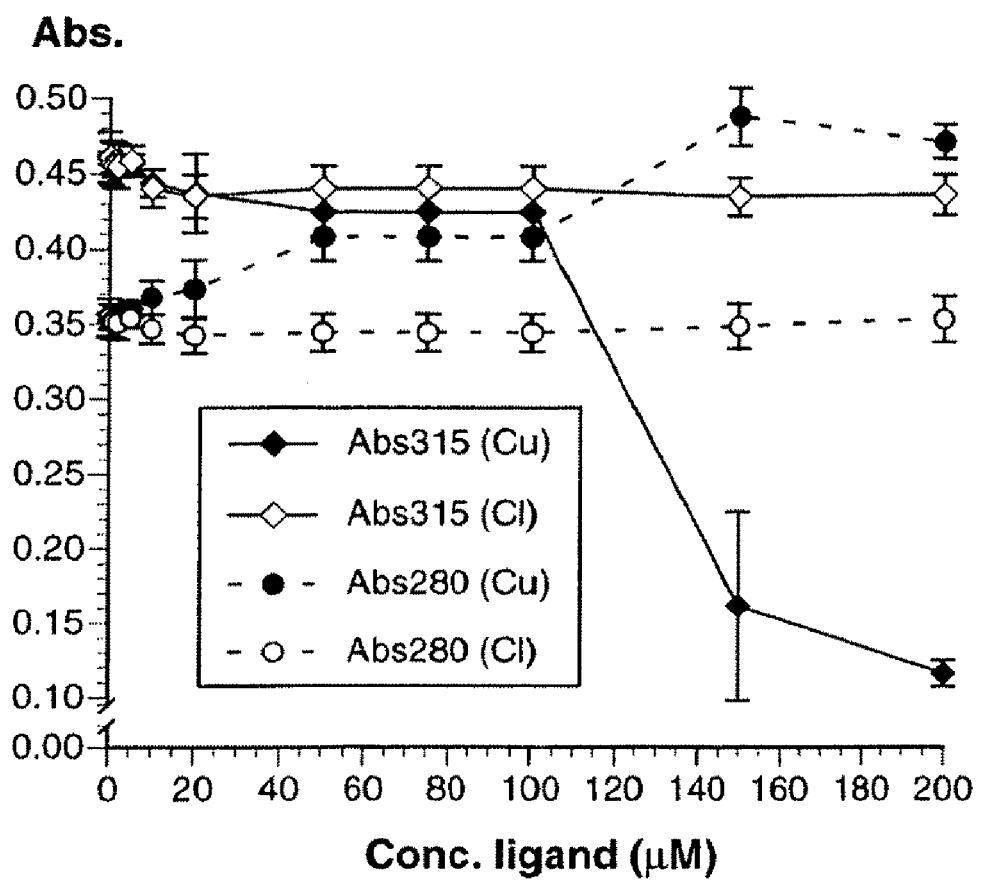

We found that as DT was incubated with increasing concentrations of $Cu^{2+}$ its characteristic absorbance peak at 315 nm diminished, whereas a new absorbance peak developed at 280 nm. The spectroscopic changes reached a plateau at a stoichiometric ratios between 1:1-2:1 (Cu:DT), and then saturated at 3:1, suggesting that DT can bind up to 3 equivalents of Cu. Dichloride binding would also produce a similar p+2 mass unit increment (Cl mass=35 and 37 Da, ≈3:1 natural isotope abundance), but coincubating DT with NaCl induced no spectroscopic absorbance changes. These results are shown in FIG. 3C.

EXAMPLE 5

Dityrosination of Aβ Increases its Copper-Binding Capacity

We predicted that a proportion oaf the Aβ found in the soluble fraction of human brain would display enhanced copper binding properties due to dityrosination. To test whether this was in fact the case, we passed a portion of soluble extract of AD-affected brain over a chelating Sepharose column charged with copper. 0.5 g of cerebral cortex grey matter from frozen AD and control brains (AC) was homogenised in 3 ml of ice cold phosphate buffered saline (PBS). Samples were centrifuged at 175 000 g for 1 hour and the supernatant retained for analysis of Aβ content. 10 ml of supernatant was loaded onto a chelating Sepharose column charged with 1 mg/ml copper sulphate. Unbound proteins were washed through using a 0.05M Na acetate buffer with 0.5M NaCl at pH 8. The bound material eluted in a stepwise gradient of increasing acidity, using successive steps of pH 5.5, 3 and 1, followed by a wash with 50 mM EDTA to strip the column. Eluates were subjected to exhaustive dialysis to remove free copper and salts using a size cutoff of 2 kDa, freeze-dried and subjected to SDS-PAGE, Western blot and LC-MS analyses. ESI mass spectra (+ve ion) were acquired on a Quatro II triple quadrupole (Micromass). Mass spectra were collected in continuum mode every 8 seconds from 650 to 1650 m/z. Samples were introduced to the ion source in 5 mM ammonium acetate buffer. Slot blot analysis showed no WO2 immunoreactivity in the pH3 eluate, and a further elution was performed at pH 1. Strong immunoreactivity was detected at this pH, and the dialysed sample was blue in colour.

Western blot analysis revealed the presence of Aβ in the pH 1 and EDTA fractions; this suggested very high-affinity binding to copper, since pH 3 is usually sufficient to elute most copper-binding protein from such a column. Material in these fractions was shown to be highly enriched in oligomeric Aβ. These results are illustrated in FIG. 4.

Figure 4B:
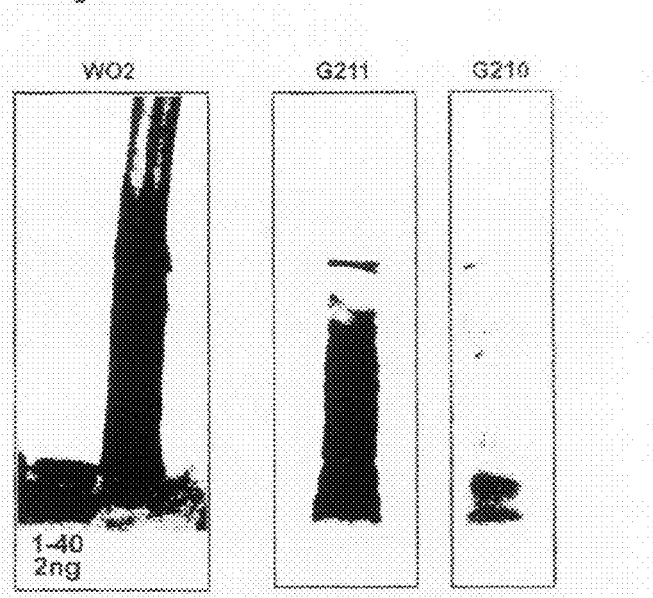

Silver staining (FIG. 4A) demonstrated substantial metal affinity-based purification (lane 1 vs. 2), and Western blot analysis displayed immunoreactive bands which appear to correspond to multiples of monomeric Aβ (FIG. 4B). FIG. 5 shows LC (top) and MS (bottom) traces from crude and IMAC-purified supernatant extracts from AD brain tissue. It is noticeable that the LC and MS spectra are substantially cleaner for the IMAC purified sample. LC-MS analysis of the IMAC purified sample produced signals corresponding to Aβ species, including $A\beta_{1-40}$ bearing 2 copper atoms, as confirmed by LC-MS analysis of synthetic peptide in the presence or absence of copper. Highlighted peak clusters on representative mass spectra indicate mass/charge ratios consistent with parent ions of masses 4515.1 ($A\beta_{1-42}$) and 4457.9 ($A\beta_{1-40}$+2 Cu).

In order to confirm whether this strongly copper-binding β fraction contained DT, we employed the monoclonal antibody IC3 raised against DT generated by a process using $H_2O_2$ and horseradish peroxidase (Kato et al. (1998); this was the gift of Dr. Yoji Kato of the Himeji Institute of Technology, Himeji, Japan). We found that the higher molecular weight oligomers of Aβ observed on Western blot co-localised with positive staining for DT.

The Aβ containing fractions also exhibited fluorescence emission spectra characteristic of the presence of the dityrosine moiety. This emission was quenched by the addition of copper in a fashion predicted for the enhanced copper binding due to this modification.

EXAMPLE 6

Further Characterisation of Dityrosinated Aβ

DT-enriched Aβ is isolated from the soluble fraction of human brain in sufficient quantity to carry out further characterisation. These studies include toxicity studies in tissue culture, amino acid sequencing, metal binding studies, and experiments to determine whether PT-enriched Aβ has enhanced electrochemical activity, for example induction of hydrogen peroxide formation and copper reduction.

EXAMPLE 7

Effect of Immunization Against Dityrosine

We attempted to raise an immune response to DT in wild-type mice. In this experiment the PT was prepared by mixing tyrosine in borate buffer with $H_2O_2$, and incubating this mixture with horseradish peroxidase, as described in the Experimental Procedures.

DT was conjugated to the carrier protein Keyhole Limpet Haemocyanin (KLH) using glutaraldehyde and according to standard protocols. An emulsion of each of DT-KLH, KLH alone or untreated tyrosine was prepared in Freund's complete adjuvant, and two animals each were inoculated intraperitoneally with an inoculum containing 100 mg of either DT-KLH, or unreacted tyrosine or KLH alone. Pre-immune serum was taken at this time. The first immune sera were collected 10 days after immunization. Two booster immunizations were given at fortnightly intervals thereafter. Blood samples were taken at each inoculation and at one week following the final boost.

An ELISA was adapted to assay the immune response to DT. We found that the immune responses to DT of the mice which were immunized with either DT-KLH or unreacted tyrosine were never greater than the responses of mice immunized with KLH alone. The DT monoclonal antibody IC3 obtained from Dr. Kato was used as a positive control, and produced a modest positive reaction against DT in this assay.

In a second experiment, two rabbits were immunized with DT-KLH in the manner described above. The ELISA results for sera produced by these animals demonstrated a moderate immune response against DT.

We also attempted to demonstrate the presence of endogenous antibodies to DT in individual sera from four human patients who were diagnosed with Alzheimer's disease by post mortem histopathology. No immunoreactivity against DT was observed in these sera by ELISA or by Western blot.

In a further experimental iteration, we examined whether the mouse or rabbit antisera raised against the DT-KLH described above, recognised DT moieties in the dimeric and higher order oligomers of Aβ extracted from human brain. Surprisingly, none of the sera demonstrated activity against DT moieties in human brain Aβ. The positive control antibody IC3 was also negative in this assay.

EXAMPLE 8

Effect of the Method of Producing Dityrosine Moieties on Immunogenicity and Antibody Reactivity We suspected that the unexpected lack of an immune response might be due to poor antigenicity of the dityrosine moieties.

To investigate this hypothesis, we prepared tyrosine cross-linked synthetic $A\beta_{1-40}$ and $A\beta_{1-42}$ by two different methods. The first method involved incubation of the Aβ peptides in borate buffer with horseradish peroxidase and $H_2O_2$, as described in the Experimental Procedures above.

In the second method, a 2.5 μM solution of Aβ was prepared in double deionised water containing 30 μM $CuCl_2$ and 200 μM $H_2O_2$, and incubated for one to five days at room temperature.

Samples of each variety of cross-linked Aβ were subjected to PAGE, and Western blotting was performed using the Aβ-specific antibody WO2 or the positive control anti-DT antibody IC3. The results of these blots are presented in FIG. 6.

The IC3 antibody detected DT in the cross-linked Aβ in both ELISA and Western blot assays. In addition, in Western blots the antibody recognised the presence of dityrosine in the DT-KLH produced in Example 7. From these results it appears that $A\beta_{1-42}$ is more efficiently cross-linked by either the borate or copper methods than is $A\beta_{1-40}$. In addition, $A\beta_{1-40}$ loses immunoreactivity to WO2 when cross-linked with the method involving copper. This may be due to greater susceptibility of the peptide to free radical damage or the modification, masking or hindering of the antibody binding site after crosslinking.

Surprisingly, it is also evident from the differential staining with IC3 that the pattern of Aβ cross-linking through dityrosine depends on the different reactions used to produce the crosslinking. The IC3 monoclonal antibody did not detect DT produced by the boric acid method, but did detect DT produced by the copper method.

Also surprisingly, the IC3 antibody detected DT cross-linking in $A\beta_{1-40}$ in preference to $A\beta_{1-42}$. This pattern is the inverse of that observed with the anti $A\beta$ antibody WO2.

These results demonstrate that the method of inducing DT cross-linking and the structure of the polypeptide being cross-linked are crucial variables in recognition of DT by an antibody. In this case, the addition of two amino acid residues to dityrosine-linked $A\beta_{1-40}$ resulted in a dramatic decrease in the ability of an anti-dityrosine antibody to bind. This result may be extrapolated to the in vivo situation, suggesting that the selection of antigen is critical to eliciting a physiologically-relevant immune response.

EXAMPLE 9

Effect of the Form of Tyrosine Cross-Link on Antibody Recognition

It was anticipated that a DT inoculum must be conjugated to a large carrier protein to provoke an immune response. Furthermore, the quality of the immune response generated would also be in part dependent upon the selection of an appropriate carrier. To examine this we selected two alternative carriers for various DT species, Bovine Serum Albumin (BSA) and Keyhole Limpet Haemocyanin (KLH).

In addition, to investigate the role of different forms of dityrosine in immuno-recognition, we prepared a crude mixture which contained variety of forms of DT, including numerous oligomers and branched forms of DT. The tyrosine cross-links in this crude mixture were created using the borate/$H_2O_2$/peroxidase method described above. The resulting DT mixture contained molecules with linkages at a variety of positions on the ring and backbone of the tyrosine molecule. Examples of the structures produced are illustrated in FIG. 7.

The crude mixture was then separated by reverse phase HPLC into fractions which contained predominantly mono-dityrosine, dityrosine, trityrosine and polytyrosine.

Two important characteristics of the oligomeric structures are that they can present multiple copies of desired antigen to improve immunogenicity and enhance the immune response, and that they can allow the presentation of alternative forms of chemical bonds between the tyrosine residues.

To investigate the nature of the tyrosine cross-links which comprise the oxidative modifications to Aβ in vivo in AD, we also prepared tyrosine cross-linked Aβ fragments. Using the same technique, we prepared molecules consisting of two or more $A\beta_{9-16}$ peptide chains cross-linked by dityrosine (structures not shown). The resultant cross-links most probably represent a racemic mixture of a variety of forms of tyrosine cross-links.

A number of the novel structures described above were characterised in Western blots using the anti-DT monoclonal IC3 or the immune serum from a rabbit which was immunized with DT-KLH (described in Example 7). These results are presented in FIG. 8.

The results demonstrated that the dimer but not the trimer of $A\beta_{9-16}$ linked to BSA was immunoreactive to both the rabbit immune serum and the monoclonal antibody IC3.

The presence of KLH was recognised by the rabbit immune serum in the blots irrespective of whether it was conjugated to an additional tyrosine cross-link antigen. Polytyrosine-BSA and polytyrosine-KLH were recognised by IC3, but the rabbit immune serum could not distinguish between KLH alone and polytyrosine-KLH.

It is clear from these results that the rabbit immunization elicited an antibody which was reactive with some forms of dityrosine but not others, as predicted from the data presented in FIG. 6.

EXAMPLE 10

Effect of Immunization with Dityrosine on Aβ Deposits in Transgenic Animals

Transgenic mouse models are available for a number of neurological disorders, including Alzheimer's disease (Games et al., 1995; Hsiao et al., 1996); Parkinson's disease (Masliah et al., 2000); familial amyotrophic lateral sclerosis (ALS) (Gurney et al., 1994); Huntington's disease (Reddy et al., 1998); and Creutzfeld-Jakob disease (CJD) (Telling et al., 1994).

We have found that one of the transgenic models for Alzheimer's disease, the APP2576 μg mouse (Hsiao et al., 1996) also has a high incidence of cataract. These animal models are suitable for testing the methods of the invention.

Transgenic mice of the Strain APP2576 (Hsiao et al 1996) are used. Eight to nine month old female mice are selected and divided into groups for treatment.

Tyrosine cross-linked antigens are prepared using a variety of techniques to generate different forms of tyrosine cross-links. Antigens used include:

| Antigen | Carrier protein |
|---|---|
| $A\beta_{9-16}$ dimer | BSA |
| $A\beta_{9-16}$ trimer | BSA |
| (crude) ATEE | BSA |
| poly-tyrosine | BSA |
| Aβ trimer | KLH |
| (crude)ATEE | KLH |
| poly-tyrosine | KLH |

Each immunisation comprises 25 μg of antigen in Freund's complete adjuvant, in a total volume of 0.5 ml, given subcutaneously.

Control animals received carrier protein without the tyrosine cross-linked antigen.

Samples of serum are taken at 14 day intervals, with booster immunizations given at 28 days. Serum samples are assayed for the presence of anti-DT antibody, using the ELISA method of Kato et al for example. It is expected that high antibody titres are obtained by about five weeks following the final booster injection. The levels of Aβ in the blood are also determined.

Once high titre antibody is present, mice are sacrificed at intervals, and their brains examined to determine whether the immunization decreases brain amyloid formation, and to identify the most effective immunization protocol. The levels of soluble and insoluble Aβ in the brain and serum is determined using calibrated Western blots. The Aβ plaque burden in the brain is examined immunohistochemically.

Other mice in each group are tested over a period of up to eight months for cognitive performance using a Morris water maze according to standard methods. The general health and well being of the animals is also measured every day by a blinded operator using a five point integer scale that subjec-

EXAMPLE 11

Effect of Treatment with Antibodies Against Dityrosine

Normal mice are hyperimmunized by standard procedures well known in the art with one or more of the immunogens described in Example 7. The mice are bled at intervals and their sera assayed for anti-DT as described above. Upon detection of high titre antibody, sera are harvested and the antibody component isolated and/or enriched using methods commonly available in the art.

These antibodies are injected intravenously or directly into the CSF of APP2576 transgenic mice, either inn a single dose or repeated dosages over a course of days or weeks.

The transgenic mice are sacrificed at intervals following treatment with anti-dityrosine antibodies, and their brains examined to determine whether antibody treatment decreases brain amyloid formation.

EXAMPLE 12

Diagnosis of Conditions Associated with Tyrosine Cross-Linking

Samples of sera and cerebrospinal fluid (CSF) from patients confirmed to be suffering from AD and from age-matched controls are assayed for the presence of tyrosine cross-linked compounds using fluorescence analysis as described above. In one set of samples, tyrosine cross-linked compounds in the sample are first enriched by passing the sample over a solid support coupled to nitrilotriacetic acid, as described in U.S. Pat. No. 5,972,674.

Similar assays are performed using samples from patents suffering from ALS, Parkinson's disease, and CJD.

It is possible that patients may also have circulating antibodies directed against tyrosine cross-linked compounds, and so in an alternative assay such antibodies are directed in either sera or CSF using an ELISA assay, employing monoclonal antibodies directed against DT (Kato et al., 1998).

EXAMPLE 13

Identification of the Forms of Dityrosine Present in Oxidatively-Modified Aβ

In order to identify the predominant form or forms of DT present in oxidatively modified Aβ, enzymatic digestion fragments of copper-catalysed Aβ oligomers are generated, and the fragments analysed by mass spectrometry. This technique has recently been applied to the analysis of copper-catalysed oxidative modifications to the prion protein (Requena, J. R., et al. 2001 PNAS 98: 7170-7175)

This enables the identification of the antigen most likely to be effective in eliciting monoclonal antibodies suitable for use in passive immunization, as described in Example 11. Methods for generating highly specific monoclonal antibodies against any specific antigen are well known in the art. Once the antigen has been selected, a systematic analysis of the most effective means of antigen presentation is carried out using known methods.

DISCUSSION

The neuronal damage in AD is associated with soluble Aβ rather than insoluble Aβ which is immobilised in neuritic plaques (McLean et al., 1999). We have now shown for the first time that the neurotoxic Aβ oligomers extracted from AD-affected brains contain tyrosine cross-links), which may be DT, iso-DT, TT and/or P. These modifications were emulated in vitro by incubating Aβ with peroxidase and $H_2O_2$, or by oxidation of Aβ in the presence of copper ions. These modifications could interfere with the metabolism of Aβ, may contribute to the neurotoxicity seen in AD, and is indicative of the neurochemical derangement in the disease.

The formation of the carbon-carbon bridge between DT, T and P is thought to be irreversible; UT cross-links are very resistant to hydrolytic cleavage by 6N HCl at 110° C. for 24 h, and to protease digestion (Smail et al., 1995). Pathologically, the catabolic resistance of UT modifications of proteins could explain the contribution of tyrosine polymers to lipofuscin formation (Kato et al., 1998), and to the cross-linking of α-crystallin in fluorescent cataract formation (Kikugawa et al., 1991). Clearly, tyrosine cross-linkage of Aβ would be expected to inhibit its catabolism, and so may be an important step in the evolution of amyloid plaque deposits in AD.

The formation of tyrosine cross-links necessitates that molecules containing tyrosyl radicals come into contact. Our results suggest that the tyrosine residue of Aβ must be accessible to peroxidase (s), and that tyrosyl residues between Aβ subunits of amyloid must, at some stager be in apposition.

Since $H_2O_2$ is required for UT formation, the detection of DT modifications in AD-derived brain Aβ implies that $H_2O_2$ is elevated in the brain in AD. Without wishing to be bound by, any proposed mechanism, we believe that phagocytic activation of the microglial cells in the brain parenchyma, which is closely associated with amyloid formation in AD (Sheng et al., 1997), could contribute peroxidase activity and $H_2O_2$ to cause tyrosine cross-linkage of Aβ. Activated rat microglia have been observed to have increased peroxidase levels (Lindenau et al., 1998), and in vitro experiments have demonstrated the capacity of Aβ to prime and/or trigger the respiratory burst of cultured rat microglia and human phagocytes (Van Muiswinkel et al., 1996). Activated phagocytes release myeloperoxidase (Pember et al., 1983), and generate reactive oxygen species during the respiratory burst. This response is designed to kill invading pathogens or tumor cells; however, this environment has also been shown to promote the oxidation of surrounding proteins and lipids (Byun et al., 1999). A similar microenvironment may be generated in the vicinity of activated microglia. In vitro, myeloperoxidase-$H_2O_2$ systems promote the synthesis of tyrosine cross-linked species such as DT, TT, P and isoDT (Jacob et al., 1996).

Thus the activation of microglia in response to Aβ accumulation may promote tyrosine cross-linkage of the Aβ, inhibiting its clearance and leading to a vicious cycle. Contributing to this possible vicious cycle, a proximate source of $H_2O_2$ for DT formation may be generated by Aβ itself, since Aβ forms $H_2O_2$ by reacting with $O_2$ through the reduction of substoichiometric amounts of $Cu^{2+}$ or $Fe^{2+}$ (Huang, Atwood, et al., 1999; Huang, Cuajungco, et al., 1999). Therefore, it is highly significant that Aβ was purified intact, together with bound copper, from human amyloid (FIG. 3A). Synthetic $Aβ_{1-42}$ binds $Cu^{2+}$ with attomolar affinity, and since-copper is enriched in AD amyloid (Lovell et al., 1998), we had suspected that Aβ might bind copper in vivo. The finding that amyloid-derived Aβ contains copper is also relevant to Aβ pathophysiology, because $Cu^{2+}$ precipitates Aβ (Atwood et al., 1998), and the toxicity of the peptide is potentiated by $Cu^{2+}$ (Huang, et al., 1999).

Intriguingly, $Cu^{2+}$ remained bound to DT after acid hydrolysis of the human amyloid-derived Aβ, as well as under the acidic conditions of the mass spectrometry (FIG. 3A).

This unusual affinity for $Cu^{2+}$ could be the result of an adventitious high-affinity $Cu^{2+}$ binding site on Aβ being formed by the DT modification. As a consequence of this exaggerated affinity for $Cu^{2+}$, the neurotoxicity of DT-modified Aβ or its electrochemical activity may be increased compared to non-modified Aβ. Adventitious $Cu^{2+}$ binding caused by the DT modification could also exaggerate the precipitation of Aβ into amyloid, which would explain why treatment with chelators at pH 7.4 promoted the release of dimeric AZ to a greater extent than that of monomeric AZ (assayed by Western blot) from post-mortem AD brain tissue (Cherny et al., 1999). The combination of increased proteolytic resistance and adventitious metal binding may be particularly pernicious consequences of the tyrosine cross-linking of Aβ which contribute to the pathology of AD.

PDAPP transgenic mice overproduce the human form of $Aβ_{1-42}$ and show extensive cerebral amyloid plaque deposition with aging, as well as behavioural and cognitive deficits (Games et al., 1995; WO96/40896). Immunisation of mature PDAPP mice with synthetic $Aβ_{1-42}$ results in a striking diminution in the number and intensity of amyloid plaques, while PDAPP mice immunised with this antigen fail to develop amyloid plaques (Schenk et al., 1999 and WO99/27944). It appeared that a successful immune response to $Aβ_{1-42}$ had been induced, with evidence of scavenging microglial cells in the immediate vicinity of the remnant amyloid plaques, and the presence in blood of antibodies directed against $Aβ_{1-42}$. The authors suggested that immunization with Aβ could be used for prevention or treatment of AD. However, it is widely thought that it is unlikely that an immunotherapy for AD is feasible, because a human recipient would be unable to mount a significant immune response to a self protein because of immunological tolerance. The results obtained by Schenk et al. suggest that the brain may have the capacity to resorb and clear otherwise intractable amyloid deposits, given the appropriate stimulus. However, it is undesirable to use immunisation with Aβ itself, because of the potential for induction of harmful autoimmune responses, and/or the induction of an inadequate, non plague-clearing response. By immunising with non-native dityrosine or dityrosine-containing compounds according to the present invention, this problem can be avoided.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Amado, R., Aeschbach, R., and Neukom, H. (1984) *Methods Enzymol* 107, 377-88.13

Atwood, C. S., Huang, X., Moir, R. D., Scarpa, R. C., Bacarra, N. M. B., Hartshorn, M. A., Goldstein, L. B., Romano, D. M., Tanzi, R. E., and Bush, A. I. (1997) *Soc. Neurosci. Abstr.* 23, 1883

Atwood, C. S., Moir, R. D., Huang, X., Bacarra, N. M. E., Scarpa, R. C., Romano, D. M., Hartshorn, M. A., Tanzi, R. E., and Bush, A. I. (1998) *J. Biol. Chem.* 273, 12817-12826

Atwood, C. S., Scarpa, R. C., Huang, X., Parrag, Y. W., Moir, R. D., Cuajungco, M. P., Tanzi, R. E., and Bush, A. I. (1999) *Soc. Neuroscl. Abstr.* 24, 546

Atwood, C. S., Scarpa, R. C., Huang, X., Moir, R. D., Jones, W. D., Fairlie, D. P., Tanzi, R. E., and Bush, A. I. (2000) *J. Neurochemistry* 75, 1219-1233

Burdick, D., Soreghan, B., Kwon, M., Kosmoski, J., Knauer, M., Henschen, A., Yates, J., Cotman, C., and Glabe, C. (1992) *J. Biol. Chem.* 267, 546-554

Byun, J., Henderson, U. P., Mueller, D. M., and Heinecke, J. W. (1999) *Biochemistry* 38(8), 2590-600

Cherny, R. A., Legg, LT. T., McLean, C. A., Fairlie, D., Huang, X., Atwood, C. S., Beyreuther, K., Tanzi, R. E., Masters, C. L., and Bush, A. I. (1999) *J. Biol. Chem.* 274, 23223-23228

Dyrks, T., Dyrks, E., Hartmann, T., Masters, C., and Beyreuther, K. (1992) *J. Biol. Chem.* 267, 18210-18217

Galeazzi, L., Ronchi, P., Franceschi, C., and Giunta, S. (1999) *Amyloid* 6(1), 7-13

Glenner, G. G., and Wong, C. W. (1984) *Biochem. Biophys. Res. Commun.* 120, 885-890

Gross, A. J., and Sizer, I. W. (1959) *J. Biol. Chem.* 234, 1611-1614

Hsiao, K., Chapman, P., Nilsen, S., Eckman, C., Harigaya, Y., Younkin, S., Yang, F., Cole, G. Correlative memory deficits, Aβ elevation, and amyloid plaques in transgenic mice. (1996) *Science;* 274(5284):99-102.

Heinecke, J. W., Li, W., Francis, G. A., and Goldstein, J. A. (1993) *J Clin Invest* 91(6), 2866-72

Hensley, K., Maidt, M. L., Yu, Z., Sang, H., Markesbery, W. R., and Floyd, R. A. (1998) *J. Neurosci* 18 8126-8132

Huang, X., Cuajungco, M. P., Atwood, C. S., Hartshorn, M. A., Tyndall, J., Hanson, G. R., Stokes, K. C., Leopold, M., Multhaup, G., Goldstein, L. E., Scarpa, R. C., Saunders, A. J., Lim, J., Moir, R. D., Glabe, C., Bowden, E. F., Masters, C. L., Fairlie, D. P., Tanzi, R. E., and Bush, A. I. (1999) *J. Biol. Chem.* 274, 37111-6

Huang, X., Atwood, C. S., Hartshorn, M. A., Multhaup, G., Goldstein, L. E., Scarpa, R. C., Cuajungco, M. P., Gray, D. N.; Lim, J., Moir, R. D., Tanzi, R. E., and Bush, A. I. (1999) *Biochemistry* 38, 7609-7616

Jacob, J. S., Cistola, D. P., Hsu, F. F., Muzaffar, S., Mueller, D. M., Hazen, S. L., and Heinecke, J. W. (1996) *J Biol Chain* 271(33), 19950-6

Kato, Y., Maruyama, W., Naoi, M., Hashizume, Y., and Osawa, T. (1998) *FEBS Letters* 439 (3), 231-4

Kikugawa, K., Kato, T., Beppu, M., and Hayasaka, A. (1991) *Biochim Diophys Acta* 1096(2), 108-14

Lindenau, J., Noack, H., Asayama, K., and Wolf, G. (1998) *Glia* 24(2), 252-6

Lovell, M. A., Robertson, J. D., Teesdale, W. J., Campbell, J. L., and Markesbery, W. R. (1998) *J Neurol Sci* 158(1), 47-52.15

Malencik, D. A., Sprouse, J. F., Swanson, C. A., and Anderson, S. R. (1996) *Anal Biochem* 242(2), 202-13

Masters, C. L., Multhaup, G., Simms, G., Pottgiesser, J., Martins, R. N., and Beyreuther, K. (1985) *The EMBO Journal* 4, 2757-2763

McLean et al., (1999), *Ann. Neurol.* 46, 860-866.

Pember, S. O., and Kinkade, J. M., Jr. (1983) *Blood* 61(6), 1116-24.14

Requena, J. R., et al. (2001) *PNAS* 98, 7170-7175)

Roher, A. E., Chaney, M. O., Kuo, Y. M., Webster, S. D., Stine, W. B., Haverkamp, L. J., Woods, A. S., Cotter, R. J., Tuohy, J. M., Krafft, G. A., Bonnell, B. S., and Emmerling, M. R. (1996) *J Biol Chem* 271(34), 20631-5

Sela M. and Arnon, R. (1960) *Biochem J.* 75, 91-102.

Sheng, J. G., Mrak, R. E., and Griffin, W. S. (1997) *Acta Neuropathol* (Berl) 94(1), 1-5

Schenk, D. et al., (1992) *Nature* 400, 173-177.

Shivers, B. D., Hilbich, C., Multhaup, G., Salbaum, M., Beyreuther, K., and Seeburg, P. H. (1988) *EMBO J.* 7, 1365-1370

Shoji, M., Golde, T. E., Ghiso, J., Cheung, T. T., Estus, S., Shaffer, L. M., Cai, X.-D., McKay, D. M., Tintner, R., Frangione, B., and Younkin, S. G. (1992) *Science* 258, 126-129

Smail, E. H., Briza, P., Panagos, A., and Berenfeld, L. (1995) *Infect Immun* 63(10), 4078-83

Souza, J. M., Giasson, B. I., Chen, Q., Lee, V. M-Y., and Ischiropoulos (2000) *J. Biol. Chem.*, 295, 18344-18349

Van Muiswinkel, F. L., Veerhuis, R., and Eikelenboom, P. (1996) *J. Neurochem.* 66, 2468-2476

Vaughan, D. W., and Peters, A. (1981) *J. Neuropathol. Exp. Neurol.* 40, 472-487

What is claimed is:

1. A method for treating Alzheimer's disease in a subject, comprising administering to said subject an antibody or antigen-binding fragment thereof specific for an immunogenic portion of an oligomeric form of Aβ wherein said oligomeric form of Aβ is oligomeric human Aβ 9-16 comprising a covalent tyrosine crosslinked moiety linking monomers of said Aβ9-16 to form said oligomeric form of Aβ9-16.

* * * * *